(12) United States Patent
Oppenheimer et al.

(10) Patent No.: US 9,642,926 B2
(45) Date of Patent: May 9, 2017

(54) COMPOSITIONS USEFUL FOR TARGET, DETECTION, IMAGING AND TREATMENT, AND METHODS OF PRODUCTION AND USE THEREOF

(75) Inventors: Les Oppenheimer, Kinnelon, NJ (US); Ismayil M. Guracar, Redwood City, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 820 days.

(21) Appl. No.: 13/822,927

(22) PCT Filed: Sep. 26, 2011

(86) PCT No.: PCT/US2011/053249
§ 371 (c)(1),
(2), (4) Date: Mar. 13, 2013

(87) PCT Pub. No.: WO2012/047582
PCT Pub. Date: Apr. 12, 2012

(65) Prior Publication Data
US 2013/0183234 A1    Jul. 18, 2013

Related U.S. Application Data

(60) Provisional application No. 61/387,137, filed on Sep. 28, 2010.

(51) Int. Cl.
| | | |
|---|---|---|
| A61K 9/00 | (2006.01) | |
| A61K 49/22 | (2006.01) | |
| A61K 41/00 | (2006.01) | |
| A61K 47/48 | (2006.01) | |
| A61K 49/00 | (2006.01) | |
| A61K 51/04 | (2006.01) | |

(Continued)

(52) U.S. Cl.
CPC ............ *A61K 49/221* (2013.01); *A61K 31/00* (2013.01); *A61K 41/0028* (2013.01); *A61K 41/0052* (2013.01); *A61K 47/48723* (2013.01); *A61K 47/48753* (2013.01); *A61K 47/48869* (2013.01); *A61K 49/0002* (2013.01); *A61K 49/085* (2013.01); *A61K 49/16* (2013.01); *A61K 49/223* (2013.01); *A61K 49/227* (2013.01); *A61K 51/0495* (2013.01); *A61K 51/10* (2013.01); *B82Y 5/00* (2013.01)

(58) Field of Classification Search
CPC .................................................. A61K 49/221
See application file for complete search history.

(56) References Cited

U.S. PATENT DOCUMENTS

| | | |
|---|---|---|
| 7,078,015 B2 | 7/2006 | Unger |
| 2003/0129136 A1 | 7/2003 | Lanza et al. |

(Continued)

FOREIGN PATENT DOCUMENTS

SE    WO 2004090165 A1 *  10/2004  ....... G01N 33/54373

OTHER PUBLICATIONS

Kitchcock et al, Ultrasound-enhanced delivery of targeted echogenic liposomes in a novel ex vivo mouse aorta model, Journal of Controlled Release, 2010, 144, 288-295.*

(Continued)

*Primary Examiner* — Paul Dickinson

(57) ABSTRACT

Compositions useful for target detection, imaging and treatment, as well as methods of production and use thereof, are disclosed herein.

12 Claims, 7 Drawing Sheets

(51) Int. Cl.
*B82Y 5/00* (2011.01)
*A61K 49/08* (2006.01)
*A61K 49/16* (2006.01)
*A61K 51/10* (2006.01)
*A61K 31/00* (2006.01)

(56) References Cited

U.S. PATENT DOCUMENTS

2004/0141922 A1 7/2004 Klaveness et al.
2007/0092558 A1 4/2007 Heavner et al.

OTHER PUBLICATIONS

Lanza, G.M., et al. *A Novel Site-Targeted Ultrasonic Contrast Agent with Broad Biomedical Application*, Circulation. 1996, vol. 94, pp. 3334-3340.
Stieger, S.M., et al., *Imaging of angiogenesis using CadenceTM contrast pulse sequencing and targeted contrast agents*, Contrast Media Mol. Imaging 2008, vol. 3, pp. 9-18.
PCT Search Report dated Apr. 10, 2012, 16 pages total.
Translation of Office Action from counterpart Japanese application No. 2013-531697, 5 pages total dated Jun. 16, 2014.
EP Search Report dated Aug. 22, 2016 in counterpart EPO application No. 11831243.8-1453, 8 pages total.

* cited by examiner

Contrast Pulse Sequencing is sensitive to cubic nonlinearity at the fundamental imaging frequency. Tissue attenuation 0.5 dB/cm-MHz

FIG. 6

Amplification and plane bounded sphere packing

A. Single stage amplification – up to a factor of 9

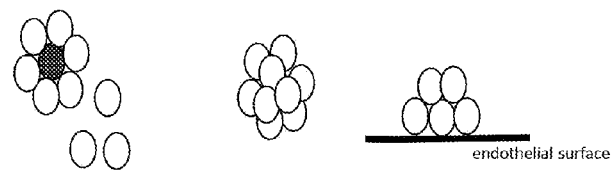

Top view—
6 gas bubbles
1 targeting
liposome
prior to adhesion
of the final 3 gas
bubbles Top view—
after adhesion
of
all bubbles Side view—
after adhesion of
all bubbles

B. Two stage amplification – up to a factor of 28

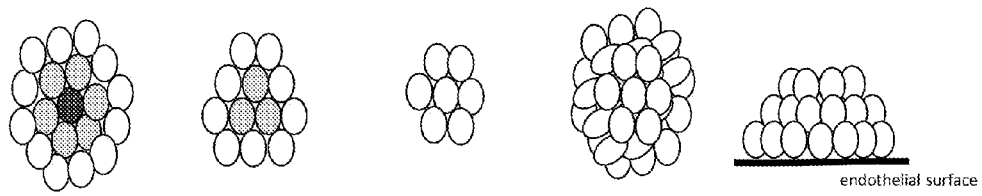

first row—
12 gas bubbles
6 amplification
liposomes
1 targeting
liposome second row—
9 gas bubbles
3 amplification
liposomes third row—
7 gas bubbles Top view—
after adhesion
of
all bubbles Side view—
after adhesion
of
all bubbles

BIACORE™ DOSE RESPONSE CURVE FOR STAGE 1 BINDING

STAGE II AMPLIFICATION

| Stage | Response Units (RU) | RU Diff (final reading − initial reading) |
|---|---|---|
| I | | |
| initial reading | -11.6 | |
| final reading | 0.9 | 12.5 |
| II | | |
| initial reading | 94.1 | |
| final reading | 140.4 | 46.3 |
| | | |
| Amplification | | 3.7 |

FIG. 10
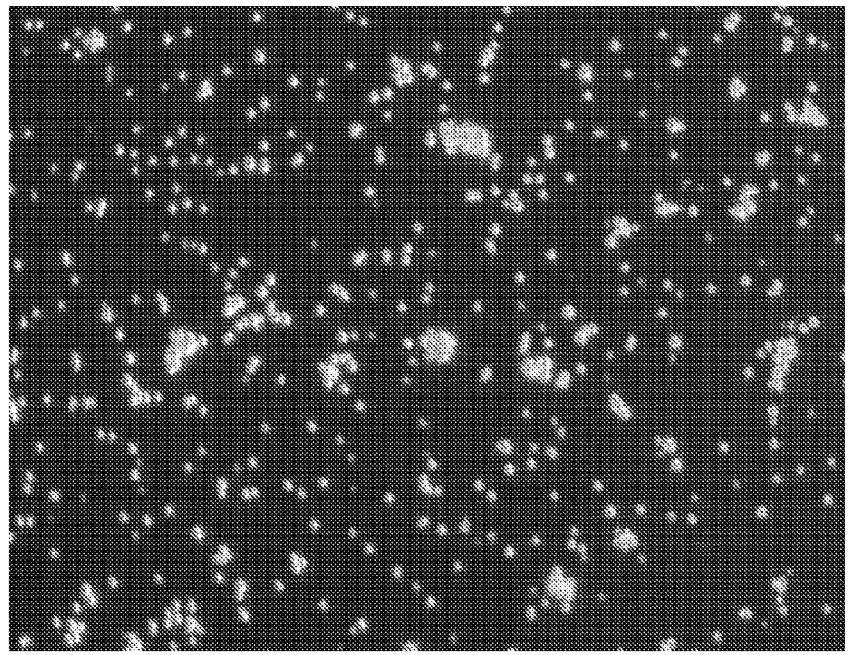
FIG. 11
Stage 1 Binding         Stage 2 Amplification
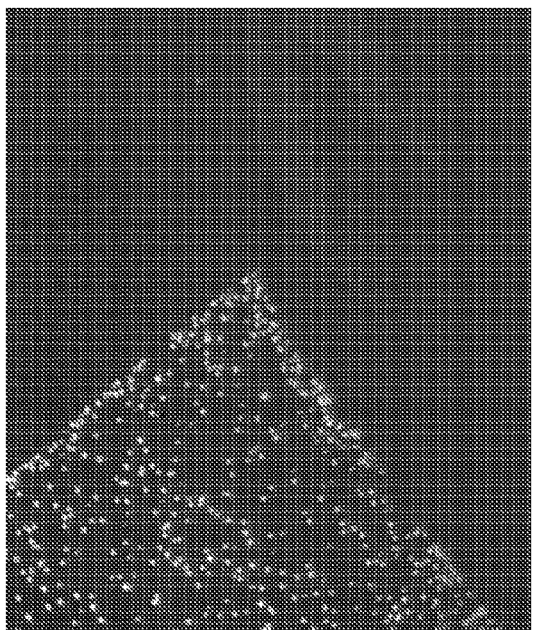     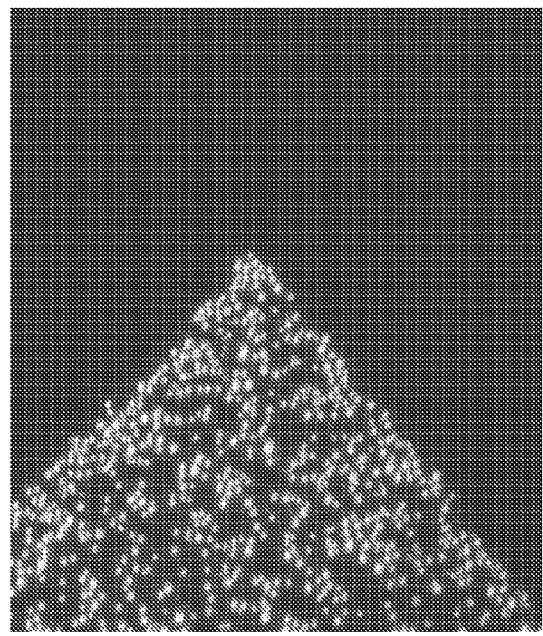

COMPOSITIONS USEFUL FOR TARGET, DETECTION, IMAGING AND TREATMENT, AND METHODS OF PRODUCTION AND USE THEREOF

CROSS REFERENCE TO RELATED APPLICATIONS

This non-provisional application is a U.S. national phase application under 35 U.S.C. 371 of International Application No. PCT/US 11/53249 filed Sep. 26, 2011, which claims the benefit of US Provisional Application Ser. No. 61/387,137, filed Sep. 28, 2010, the entire contents of which is expressly incorporated herein by reference.

STATEMENT REGARDING FEDERALLY SPONSORED RESEARCH OR DEVELOPMENT

Not Applicable.

BACKGROUND OF THE INVENTIVE CONCEPT(S)

1. Field of the Inventive Concept(s)

The presently disclosed and claimed inventive concept(s) relates generally to compositions useful in target detection and/or treatment, as well as methods of producing and using same.

2. Description of the Background Art

Targeted microbubbles are an important and emerging ultrasound molecular imaging and therapy tool. Many disease states such as but not limited to, cancer, inflammation and thrombosis have unique expression of proteins on the surface of the vascular lumen.

Lanza et al. (1996) describe the sequential delivery of a biotinylated biomarker, avidin, and perfluorocarbon emulsion. In U.S. Pat. No. 7,186,399, Lanza et al. describe an in vivo or in vitro method for ligand-based binding of lipid encapsulated particles to molecular epitopes on a surface. This is accomplished by the sequential delivery of a site specific ligand activated with biotin activating agent, an avidin activating agent, and lipid encapsulated particles activated with a biotin activating agent.

The simultaneous delivery of targeted higher order aggregates of contrast agents has also been described in the literature. These higher order aggregates employ microbubbles, liposomes, nanoparticles, bubble liposomes, liposomal bubbles, nanostructured materials, supramolecular aggregates, quantum dotes, nanotubes, and micelles in various combinations. Many of these particles are multi-modal and have therapeutic properties. See for example, Lentacker et al. (2010); Suzuki et al. (2007 and 2008); Myhr et al. (2006); Tinkov et al. (2009); Kheirolomoom et al. (2007); Huang (2008); Kim et al. (2009); Cai et al. (2008); Accardo et al. (2009); Ghaleb et al. (2008); Husseini et al. (2008); Schroeder et al. (2009); McCarthy et al. (2008); U.S. Pat. No. 7,078,015. The entire contents of each of the above-referenced patents and publications are hereby expressly incorporated by reference herein.

Unfortunately, typical adhesion rates of microbubbles retained at the target site are low (on the order of 10 microbubbles per microliter of tissue (Dayton, 2009)), even with the addition of acoustic radiation force. In particular, Dayton (2009) listed the following limitations for targeted contrast agent technology: (1) the low number of contrast agents adherent to a target site; (2) lack of sensitivity to small numbers of contrast agents; and (3) the high background from circulating untargeted contrast. These limitations are discussed in greater detail herein below.

While targeted ultrasound contrast agents demonstrate good specificity to disease, the diagnosis of disease states is limited by the sensitivity attainable by imaging technologies. When contrast agents target specific sites, they are limited to the number of binding sites available on the endothelial surface of the lumen, and therefore one binding site only allows binding of a single microbubble. In addition, the interaction of the microbubble with sites on the endothelial surface is limited by the shear forces created by blood flow through the lumen; thus, the microbubble cannot bind to a surface that it does not "touch" (i.e., with which it comes into contact). Therefore, the prior art methods result in typical binding levels of about 10 microbubbles per microliter.

Further technical limitations of the prior art reside in the imaging equipment: depth and frequency dependent attenuation is seen with ultrasound, and at high power imaging, the high peak negative pressures result in burst microbubbles. In addition, similar depth limitations are seen with other imaging modalities, such as but not limited to, MRI and PET.

Therefore, there is a need in the art for new and improved agents useful in targeted imaging and/or treatment. It is to such compositions, as well as methods of producing and using same, that the presently disclosed and claimed inventive concept(s) is directed.

BRIEF DESCRIPTIONS OF THE DRAWINGS

Figure 3:
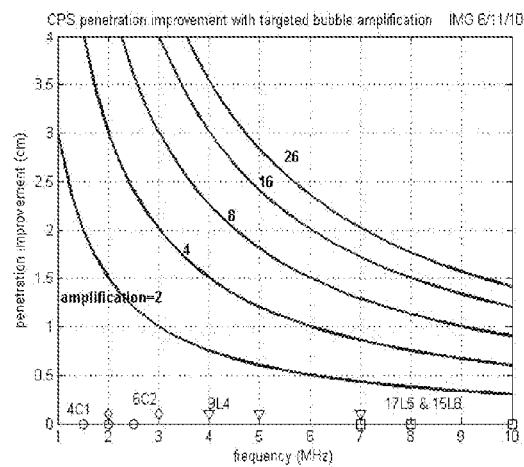

FIG. 3 graphically depicts that amplification improves contrast agent imaging penetration.

Figure 4:
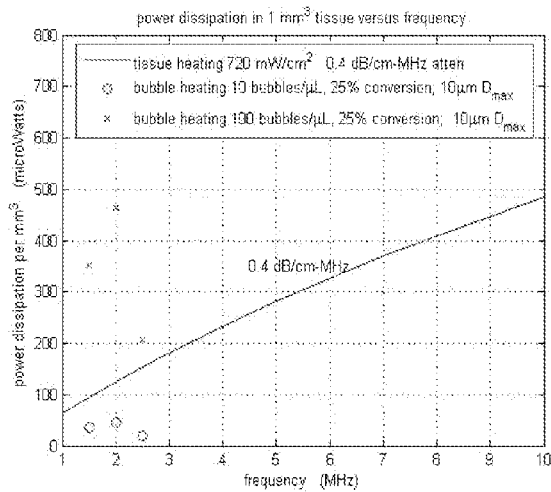

FIG. 4 graphically depicts the power dissipation in 1 mm$^3$ of tissue versus frequency.

Figure 5:
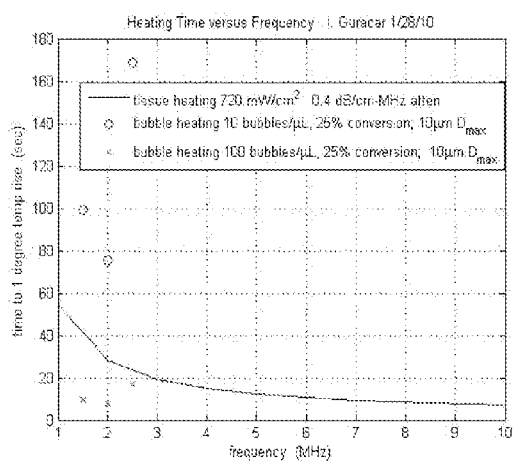

FIG. 5 graphically depicts heating time versus frequency.

FIG. 6A graphically depicts single stage amplification of a single targeting liposome. The targeting liposome (Stage I agent) is shown in black.

FIG. 6B graphically depicts a second stage of amplification of a single targeting liposome. The single targeting liposome is shown in black, and the nine adhering amplification liposomes (Stage II agents) are shown in grey. Twenty eight imaging liposomes (Stage III agents) that form the final adhering cluster are shown as circles without fill.

Figures 7A, 7B:
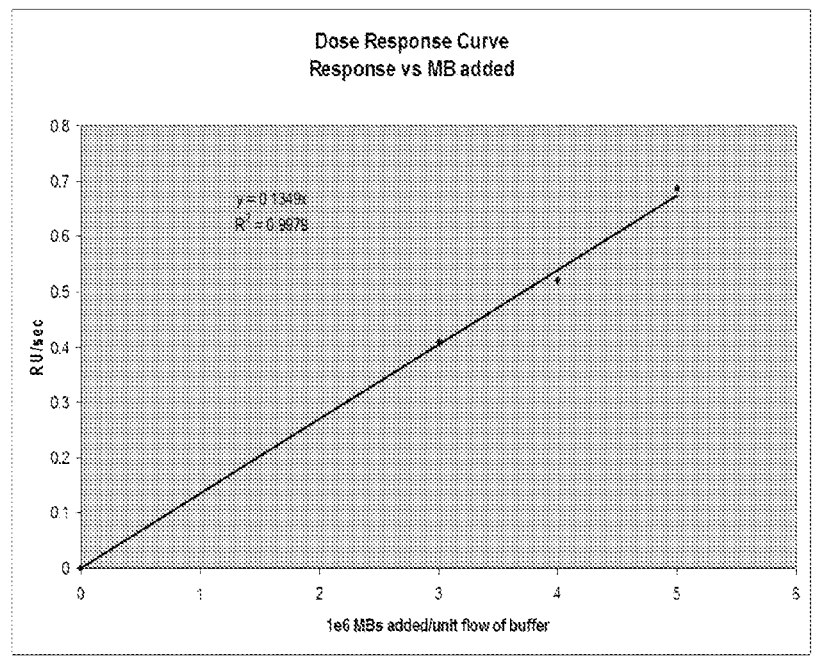

FIG. 7a illustrates a dose response curve establishing the relationship between the signal magnitude and the binding of microbubbles. The table in FIG. 7b summarizes the multistage amplification of microbubbles using BIA-CORE™ X100 Optical Biosensor.

Figure 8:
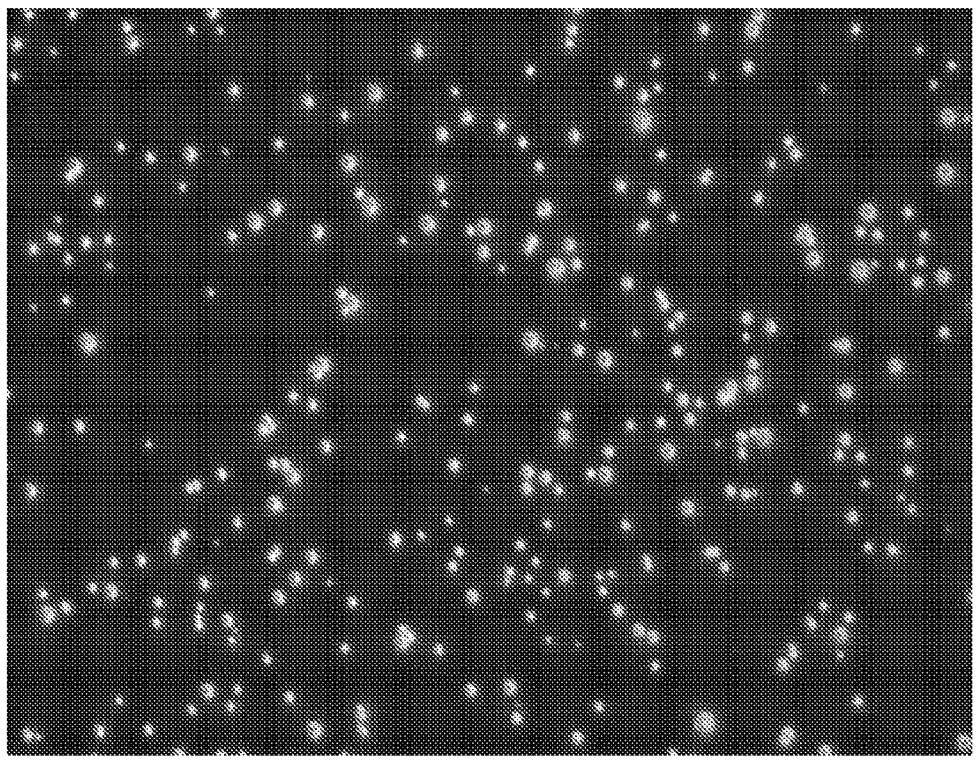
Figure 9:
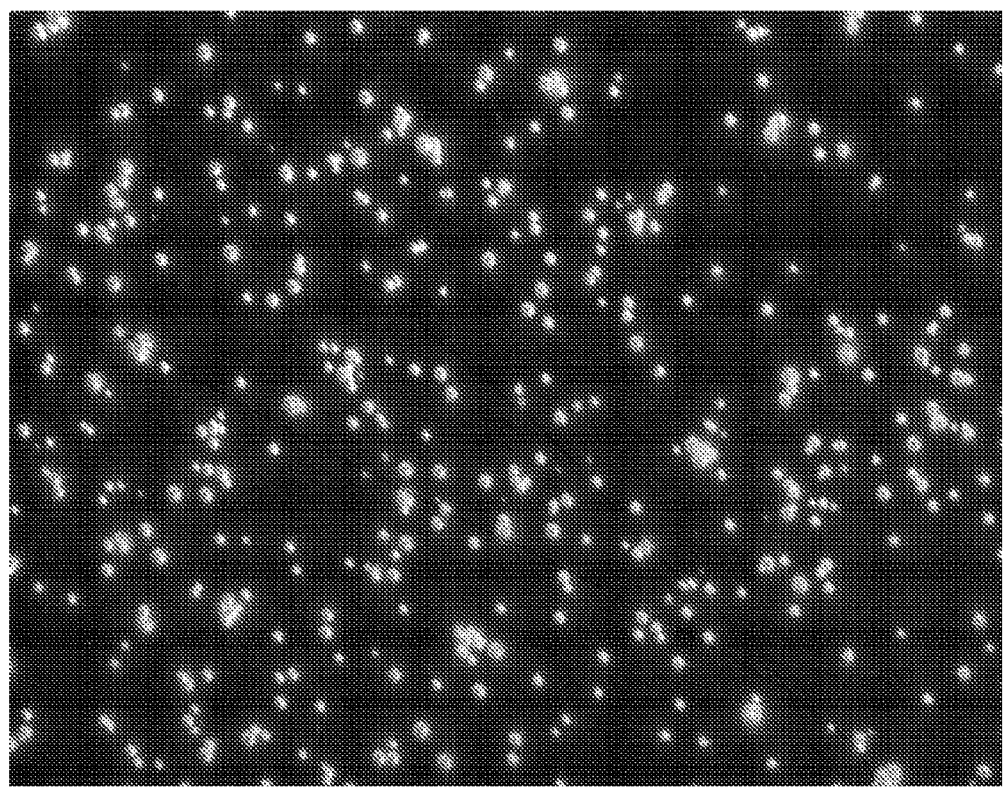

FIGS. 8-10 contain photomicrographs of dark phase confocal microscopy illustrating in vitro assembly of multistage complexes in situ. FIG. 8 illustrates Stage I binding (i.e., binding of targeting agent), FIG. 9 illustrates Stage II binding (i.e., binding of amplification agent), and FIG. 10 illustrates Stage III binding (i.e., binding of imaging agent).

FIG. 11 contains photomicrographs illustrating in vitro assembly of Stage I targeting and Stage II amplification.

DETAILED DESCRIPTION OF THE INVENTIVE CONCEPT(S)

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results.

The term "about" is used to indicate that a value includes the inherent variation of error for the device, the method being employed to determine the value and/or the variation that exists among study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

The term "combinable formulation" as used herein will be understood to refer to a mixture of components that is prepared according to a specific procedure and useful for one or more particular applications. In certain embodiments of the presently disclosed and claimed inventive concept(s), the components of the combinable formulation are not combined together prior to administration; rather, the components are provided separately and delivered serially or sequentially so that the formulation/complex is formed in situ.

The term "agent" as used herein will be understood to refer to any vehicle with a surface capable of having one or more binding sites thereon for interaction with a target and/or another agent in a lumen of a subject. In certain embodiments, the "agent" may be selected from the group consisting of vesicles, liposomes, echogenic liposomes, multimodal echogenic liposomes, microbubbles, microballoons, microspheres, matrix particles, micelles, aggregation based constructs, nanoparticles, perfluorocarbon nanodroplets, and combinations thereof.

The term "contrast agent" as used herein will be understood to a substance used to improve the resolution in highlighting an organ or tissue during imaging analysis. Contrast agents are substances used to enhance the contrast of structures or fluids within the body in medical imaging.

The term "targeted contrast agent" refers to a contrast agent that has a biomarker attached thereto that "targets" the contrast agent to a target site to which the biomarker binds.

The term "target" as used herein will be understood to refer to any moiety present on a surface of a luminal wall, wherein a targeting agent has affinity therefor and thus can bind to said moiety. The "target" may be a peptide, polypeptide, protein, epitope, antigen, receptor, complex (i.e., an MHC-peptide complex), and combinations or derivatives thereof.

The term "binding site" as used in accordance with the presently disclosed and claimed inventive concept(s) will be understood to refer to any biomolecule that has binding affinity to another substance/binding site and is capable of forming a complex therewith, thereby providing affinity between two agents/vesicles. For example but not by way of limitation, the binding sites may be peptides, proteins, antigens, antibodies, antibody fragments, receptors, ligands, glycoconjugates, and combinations or derivatives thereof. In one embodiment, the "binding site" is one of a complimentary pair (for example but not by way of limitation, biotin-avidin, antibody-antigen, etc.). Materials should, in general, be selected from a group that will not elicit an allergic response but are not ordinarily found within the test lumen. Examples of non-targeting binding sites (i.e., infrastructural binding sites utilized for binding of amplification, imaging and/or therapeutic agents to a previously targeted agent or agent complex) that may be utilized in accordance with the presently disclosed and claimed inventive concept(s) include, but are not limited to, proteins such as but not limited to creatinine-kinase-brain-type (CKBB), or therapeutic drugs such as but not limited to carbamazepine, cortisol, tobramycin, theophylline, phenytoin, vancomycin, digitoxin, digoxin, gentamycin, phenobarbital, and valproic acid, along with their corresponding humanized antibodies.

The term "polypeptide" as used herein is a generic term to refer to native protein, fragments, or analogs of a polypeptide sequence. Hence, native protein, fragments, and analogs are species of the polypeptide genus.

The term "receptor" as used herein will be understood to include a biomolecule to which one or more specific kinds of molecules (i.e., ligands) may attach. In one embodiment, the term "receptor" refers to a ligand, any peptide, protein, glycoprotein, polycarbohydrate, or lipid that is expressed on the surface of a luminal wall of an organ/tissue to be targeted and is exposed in a manner that will allow interaction with a circulating targeting agent; that is, in said embodiment, the "receptor" functions as a "target" as described in detail herein above. However, it is to be understood that any receptors known in the art or otherwise contemplated by a person of ordinary skill in the art may function as a "binding site" as described herein above.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

"Antibody" or "antibody peptide(s)" refer to an intact antibody, or a binding fragment thereof that competes with the intact antibody for specific binding. The term "antibody" is used in the broadest sense, and specifically covers monoclonal antibodies (including full length monoclonal antibodies), polyclonal antibodies, multispecific antibodies (e.g., bispecific antibodies), and antibody fragments (e.g., Fab, F(ab')2 and Fv) so long as they exhibit the desired biological activity. Antibodies (Abs) and immunoglobulins (Igs) are glycoproteins having the same structural characteristics. While antibodies exhibit binding specificity to a specific antigen, immunoglobulins include both antibodies and other antibody-like molecules which lack antigen specificity. Antibody binding fragments are produced by recombinant DNA techniques, or by enzymatic or chemical cleavage of intact antibodies. Binding fragments include Fab, Fab', F(ab')2, Fv, and single-chain antibodies. An antibody other than a "bispecific" or "bifunctional" antibody is understood to have each of its binding sites identical.

A "chimeric" antibody refers to an antibody made up of components from at least two different sources. In certain embodiments, a chimeric antibody comprises a portion of an antibody derived from a first species fused to another molecule, e.g., a portion of an antibody derived from a second species. In certain such embodiments, a chimeric antibody comprises a portion of an antibody derived from a non-human animal fused to a portion of an antibody derived from a human. In certain such embodiments, a chimeric antibody comprises all or a portion of a variable region of an antibody derived from a non-human animal fused to a constant region of an antibody derived from a human.

When antibodies are utilized in accordance with the presently disclosed and claimed inventive concept(s) and administered to a human, said antibodies may be "humanized" to prevent elicitation of an immune response thereto. A "humanized" antibody refers to a non-human antibody that has been modified so that it more closely matches (in amino acid sequence) a human antibody. The humanized antibodies are engineered such that antigenic portions thereof are removed and like portions of a human antibody are substituted therefore, while the antibodies' affinity for the desired epitope is retained. This engineering may only involve a few amino acids, or may include portions or entire framework regions, variable regions and/or complementarity determining regions (CDRs) of the antibody. A humanized antibody is thus a type of chimeric antibody. Many methods of humanizing antibodies are known in the art and are disclosed in U.S. Pat. Nos. 6,180,370, issued to Queen et al. on Jan. 30, 2001; 6,054,927, issued to Brickell on Apr. 25, 2000; 5,869,619, issued to Studnicka on Feb. 9, 1999; 5,861,155, issued to Lin on Jan. 19, 1999; 5,712,120, issued to Rodriquez et al. on Jan. 27, 1998; 5,225,539, issued to Winter on Jul. 6, 1993; and 4,816,567, issued to Cabilly et al. on Mar. 28, 1989, the Specifications of which are all hereby expressly incorporated herein by reference in their entirety. In addition, the prior art is filled with published articles relating to the generation or use of humanized antibodies. Many of these studies teach useful examples of protocols that can be utilized with the presently disclosed and claimed inventive concept(s), such as but not limited to, Sandborn et al., Gatroenterology, 120:1330 (2001); Mihara et al., Clin. Immunol. 98:319 (2001); Yenari et al., Neurol. Res. 23:72 (2001); Morales et al., Nucl. Med. Biol. 27:199 (2000); Richards et al., Cancer Res. 59:2096 (1999); Yenari et al., Exp. Neurol. 153:223 (1998); and Shinkura et al., Anticancer Res. 18:1217 (1998), all of which are expressly incorporated in their entirety by reference. The presently disclosed and claimed inventive concept(s) further includes the use of fully human monoclonal antibodies; methods of providing fully human monoclonal antibodies are well known in the art and are described, for example, but not by way of limitation, in the following: U.S. Pat. Nos. 5,545,807; 5,545,806; 5,569,825; 5,625,126; 5,633,425; 5,661,016; 5,916,771; 5,939,598; PCT publication WO 94/02602; and in the non-patent references of Kozbor, et al., Hybridoma, 2:7 (1983); Cole, et al., PNAS 82:859 (1985) Cote, et al., PNAS 80:2026 (1983); Cole, et al., (1985); Marks et al., J Biol. Chem. 267:16007 (1992); Lonberg et al., Nature, 368:856 (1994); Morrison, 1994; Fishwild et al., Nature Biotechnol. 14:845 (1996); Neuberger, Nat. Biotechnol. 14:826 (1996); and Lonberg and Huszar, Int Rev Immunol. 13:65 (1995).

However, it is to be understood that the inventive concept(s) is not limited to the protocols described above, and other protocols of producing humanized antibodies or fully human antibodies which are known to a person of ordinary skill in the art may be utilized in accordance with the presently disclosed and claimed inventive concept(s).

The term "effective amount" refers to an amount of a biologically active molecule or conjugate or derivative thereof sufficient to exhibit a detectable therapeutic effect without undue adverse side effects (such as toxicity, irritation and allergic response) commensurate with a reasonable benefit/risk ratio when used in the manner of the inventive concept(s). The therapeutic effect may include, for example but not by way of limitation, inhibiting the growth of undesired tissue or malignant cells. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The phrase "in conjunction with" when used in reference to the use of one or more agents described herein indicates that the agent(s) are administered so that there is at least some chronological overlap in their physiological activity on and/or binding to the organism. Thus the agent(s) can be administered sequentially. In sequential administration, there may even be some substantial delay (e.g., minutes or even hours or days) before administration of the second moiety, as long as the first administered agent has exerted some physiological effect on the organism and/or remains bound to the organism when the second administered agent is administered and/or becomes active in the organism.

The terms "administration" and "administering", as used herein will be understood to include all routes of administration known in the art, including but not limited to, oral, topical, transdermal, parenteral, subcutaneous, intranasal, mucosal, intramuscular and intravenous routes, including both local and systemic applications. In addition, the methods of administration may be designed to provide delayed or controlled release using formulation techniques which are well known in the art.

The term "lumen" as used herein will be understood to refer to an interior space of a biological tubular structure. Examples of lumens utilized in accordance with the presently disclosed and claimed inventive concept(s) include, but are not limited to, a vascular lumen, a spinal lumen, a lymphatic lumen, and the like.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer.

The term "metastasis" as used herein will be understood to refer to the spread of cancer from a primary tumor to other parts of the body. Metastasis is a sequential, multistep process in which tumor cells detach from a primary tumor, migrate through the basement membrane and extracellular matrix, and invade the lymphatic and/or blood systems. This is followed by the establishment of secondary tumors at distant sites.

As used herein, the term "anticancer agent" refers to a molecule or complex of molecules capable of inhibiting cancer cell function. The agent may inhibit proliferation or may be cytotoxic to cells. A variety of anticancer agents can be used and include those that inhibit protein synthesis and those that inhibit expression of certain genes essential for cellular growth or survival. Anticancer agents include those that result in cell death and those that inhibit cell growth, proliferation and/or differentiation. In one embodiment, the anticancer agent may be selectively toxic against certain types of cancer cells but does not affect or is less effective against other normal cells. In another embodiment, the anticancer agent may kill at cells equally, but the faster growing cells are killed faster. In a further embodiment, the anticancer agent is an antineoplastic agent.

The term "antineoplastic agent" is used herein to refer to agents that have the functional property of inhibiting a development or progression of a neoplasm in a human or animal, particularly a malignant (cancerous) lesion, such as a carcinoma, sarcoma, lymphoma, or leukemia. Inhibition of metastasis is frequently a property of antineoplastic agents.

The terms "patient" as used herein includes human and veterinary subjects. "Mammal" for purposes of treatment refers to any animal classified as a mammal, including human, domestic and farm animals, nonhuman primates, and any other animal that has mammary tissue.

The term "healthy patient" as used herein will be understood to refer to a patient who is free of a disease/condition/disorder being studied in a separate patient that is to be subjected to treatment.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. The present method of "treating" a patient or individual, as the term is used herein, thus encompasses both prevention of a disorder in a predisposed individual, reduction in occurrence of symptoms, and treatment of the disorder in a clinically symptomatic individual.

A "disorder" is any condition that would benefit from treatment with the compositions of the presently disclosed and claimed inventive concept(s). This includes chronic and acute disorders or diseases including those pathological conditions which predispose the mammal to the disorder in question.

As used herein, the term "treating cancer" or "treatment of cancer" means to inhibit the spread of cancer, decrease tumor size, lessen or reduce the number of cancerous cells in the body, and/or ameliorate or alleviate the symptoms associated with the cancer. The treatment is considered therapeutic if there is a decrease in mortality and/or morbidity, or a decrease in disease burden manifested by reduced numbers of malignant cells in the body.

"Preventing cancer" or "prevention of cancer" is intended to mean preventing the occurrence or recurrence of the disease state of cancer. As such, a treatment that impedes, inhibits, or interferes with metastasis, tumor growth, or cancer proliferation is deemed preventive.

As used herein, the term "managing cancer" encompasses reducing the chance of recurrence of cancer in a patient who had suffered from cancer, lengthening the time a patient remains in remission, reducing the occurrence of cancer in patients at risk of suffering from cancer (e.g., patients who had been exposed to high amounts of radiation or carcinogenic materials; patients infected with viruses associated with the occurrence of cancer; and patients with genetic predispositions to cancer), and reducing the occurrence of malignant cancer in patients suffering from pre-malignant or non-malignant cancers.

Administering a therapeutically effective amount or prophylactically effective amount is intended to provide a therapeutic benefit in the treatment, prevention, or management of a disease/disorder/condition, such as but not limited to, cancer. The specific amount that is therapeutically effective can be readily determined by the ordinary medical practitioner, and can vary depending on factors known in the art, the patient's history and age, the type and stage of the disease/disorder/condition, the co-administration of other therapeutic compositions, etc.

The term "sonoporation" as used herein will be understood to refer to the use of sound (typically ultrasonic frequencies) for modifying the permeability of the cell plasma membrane. This technique is usually used in molecular biology and non-viral gene therapy in order to allow uptake of large molecules such as DNA into the cell, thus enhancing gene or drug delivery to a cell. Sonoporation employs the acoustic cavitation (i.e., formation of empty cavities in a liquid by high forces and the immediate implosion thereof) of microbubbles to enhance delivery of these large molecules. In addition, extended exposure to low-frequency (<MHz) ultrasound has been demonstrated to result in complete cellular death (rupturing).

The term "acoustic radiation force" as used herein will be understood to refer to a physical phenomenon resulting from the interaction of an acoustic wave with an obstacle placed along its path. Generally, the force exerted on the obstacle will result in displacement of the obstacle. Acoustic radiation force is utilized as a mechanism to move a freely flowing contrast agent toward the endothelium and thus enhance contrast agent adhesion to a target surface.

The term "echogenic liposome" as used herein will be understood to refer to a liposome that comprises a gas; echogenic liposomes reflect high-frequency sound waves and thus can be imaged by ultrasound techniques. Acoustic radiation force may be utilized to move echogenic liposomes toward the endothelium and thus enhance their adhesion to a target surface. Microbubbles are a type of echogenic liposomes in which the perfluorocarbon fills the entire cavity.

The term "ablation" as used herein will be understood to refer to the use of high-intensity focused ultrasound for precise targeting of tissues for therapy (i.e., removal or destruction of tissue). The use of ultrasound ablation techniques is described in detail in Halpern (2005). Briefly, the mechanisms of tissue destruction with high-intensity focused ultrasound (HIFU) ablation are related to hyperthermia and cavitation. Low-intensity ultrasound energy, as used in diagnostic imaging, propagates harmlessly through tissue. High-intensity focused ultrasound ablation focuses an extracorporeal source of ultrasound to a specific target tissue. The ultrasound energy passes harmlessly through overlying tissues en route to a tightly focused target area. The rapid rate of energy deposition at the target tissue far exceeds the rate of heat dissipation, resulting in a rapid rate of temperature rise. While other thermal ablation techniques are limited by dissipation of heat into adjacent tissues, the rapid, focused deposition of ultrasound energy with high-intensity ultrasound ablation (0.5-1.0 seconds) produces local cavitation and temperatures of 65°-100° C. with little heating of adjacent tissues. Temperatures above 56° C. for a period of 1 second result in irreversible cell death, with a sharply defined region of tissue necrosis. The ability to focus and accurately target a lesion with high-intensity focused ultrasound by using real-time ultrasound or magnetic resonance imaging guidance allows precise ablation of lesions of any shape without damage to surrounding structures.

Turning now to the presently disclosed and claimed inventive concept(s), targeted microbubbles are an important and emerging ultrasound molecular imaging and therapy tool that provide enhanced specificity to the use of contrast agents. Many disease states such as but not limited to, cancer, inflammation and thrombosis have unique expression of proteins on the surface of the vascular lumen. The use of biomarkers attached to contrast agents enhances accumulation of the contrast agents at a specified site, thus increasing the effective signal at the site; in addition, the use of targeted contrast agents reduces the rate at which contrast agents are cleared, thus increasing the useful clinical window for imaging. However, the current state of the targeted contrast agent prior art possesses the disadvantage of limited sensitivity: the technology is limited by the number of available binding sites (i.e., one targeted imaging agent per binding site). In addition, typical adhesion rates are low (approximately 10 bubbles per microliter), even with the addition of acoustic radiation force (which typically doubles the adhesion rate), and thus binding is limited by the interaction of the targeted contrast agents with sites on the lumen.

While targeted ultrasound contrast agents demonstrate good specificity to disease, the diagnosis of disease states is limited by the sensitivity attainable by imaging technologies. When contrast agents target specific sites, they are limited to the number of binding sites available on the endothelial surface of the lumen, and therefore one binding site only allows binding of a single microbubble. In addition, the interaction of the microbubble with sites on the endothelial surface is limited by the shear forces created by blood flow through the lumen; thus, the microbubble cannot bind to a surface that it does not contact. Therefore, the prior art methods utilizing microbubbles and ultrasound result in typical binding levels of about 10 microbubbles per microliter. Similar limitations are seen with other imaging modalities, where once again said methods are limited to one imaging vesicle per binding site, and thus the number of imaging vesicles is determined by the concentration of available binding sites.

Further technical limitations of the prior art reside in the imaging equipment: depth and frequency dependent attenuation is seen with ultrasound, and at high power imaging, the high peak negative pressures result in burst microbubbles.

The presently disclosed and claimed inventive concept(s) overcomes these disadvantages and defects of the prior art by increasing the signal from a target site. This is specifically accomplished by increasing the number of bound microbubbles (or other vehicular agents) significantly, thus providing significant improvement in targeted imaging sensitivity.

In addition, the enhanced targeting and amplification functions of the presently disclosed and claimed inventive concept(s) enable the delivery of an adequate number of microbubbles (or other vehicular agents) for more efficient uses of therapeutic ultrasound, such as but not limited to, directed tissue heating, sonoporation and ablation. The increased number of targeted microbubbles in a given region of tissue enables targeted acoustic energy mediated therapy. A sufficient number of bubbles in a region of tissue will increase the conversion of acoustic energy to heat in an insonified region to an extent greater than the normal absorption of heat by the surrounding tissue. The unit absorption of ultrasound for a microbubble is more than a unit of ultrasound absorption for normal tissue. However, it is only when there is a high concentration of microbubbles in a localized area that sufficient ultrasound absorption of energy occurs to induce hyperthermia. A large region of tissue can then be insonified, and a differential heating effect based on concentrations of targeted bubbles will occur. Therapy can therefore be localized by the combination of targeting on the molecular level and directed ultrasound energy.

The term "sufficient number of bubbles" as used herein will be understood to vary depending on factors such as but not limited to, bubble size, insonation (i.e., ultrasound wave exposure) frequency and intensity, and particular application method. For example but not by way of limitation, in the case of imaging targeted agents, increases in the number of targeting bubbles increases the backscattered signal, improving signal to noise ratio. A doubling of the number of targeted bubbles within a given volume should provide an approximate doubling of the received backscattered acoustic signal. Amplification can also enhance imaging penetration. The effect is a function of frequency. At 3 MHz, for example, a two fold increase in targeted contrast agent binding will enable an additional 1 cm penetration of the acoustic signal (see FIG. 3). In another non-limiting example, in therapeutic applications where bubbles are used to convert acoustic energy to heat energy, the number of targeted bubbles must exceed a threshold to overcome the natural heating effect of acoustic energy on the surrounding tissue. Based on calculations of heating effect of bubble and tissue with an average bubble diameter of about 3 micrometers, somewhere between 20 and 100 bubbles per microliter are needed to achieve this affect. Fewer or larger numbers of bubbles may be needed depending on the physical factors listed above. For the case of targeted ablation, increases in the number of targeted bubbles will cause a greater ablation effect. In the case of targeted ischemia, a sufficient number of bubbles to cause substantial blockage in a capillary are needed. For example but not by way of limitation, with a 10 micrometer diameter capillary and using a 3 micrometer liposome, two stage amplification may be sufficient to significantly block the flow of red blood cells having a diameter of about 6-8 micrometers. As the microbubble size increases, the number of steps required to obtain partial occlusion decreases. Also, in general, the liposomes would have smaller diameters to minimize occlusion.

Heating tissue by several degrees can increase the activity of drugs and the amount of blood flow without inducing permanent tissue damage. Higher levels of heating can induce permanent tissue damage which may be of therapeutic benefit. In addition to increased heating, increases to the number of targeted bubbles can also lead to increases in other therapeutic effects such as cavitation or bubble collapse, which can be used to ablate tissue or induce sonoporation. Sonoporation is associated with increased drug and gene delivery and therapeutic benefit.

In addition to ultrasound uses, the presently disclosed and claimed inventive concept(s) also improves other imaging modalities (such as but not limited to, MRI and PET) with the unique feature that the targeting agents are confined to the lumen.

Figure 1:
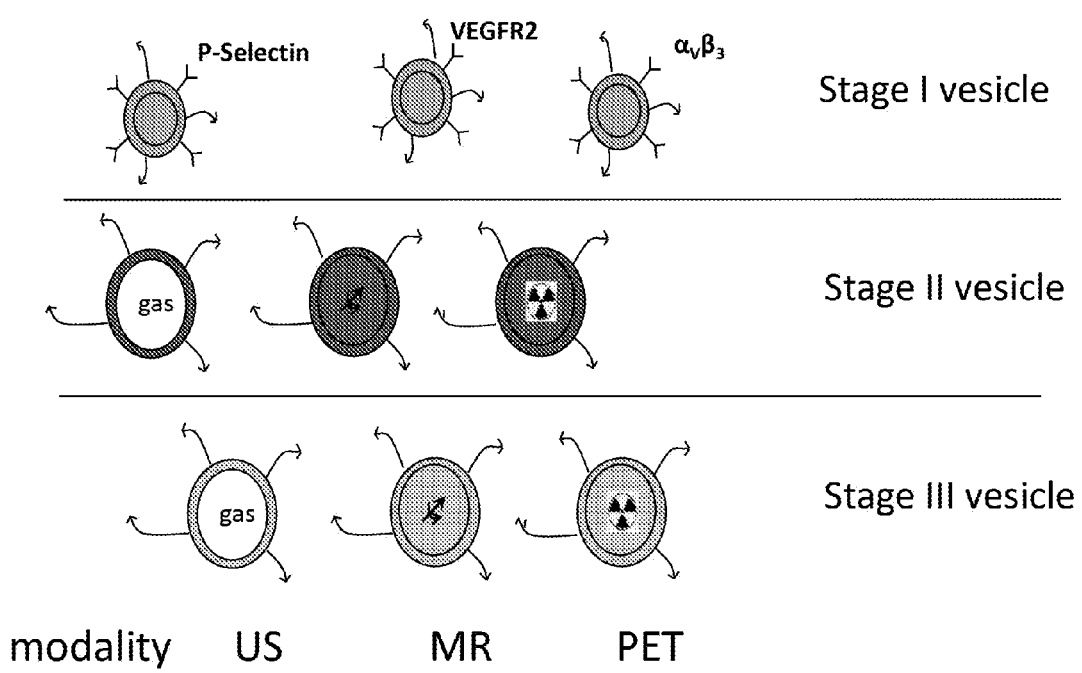
FIG. 1 depicts a universal multi-modal targeting and therapeutic system of the presently disclosed and claimed inventive concept(s).
Figure 2:
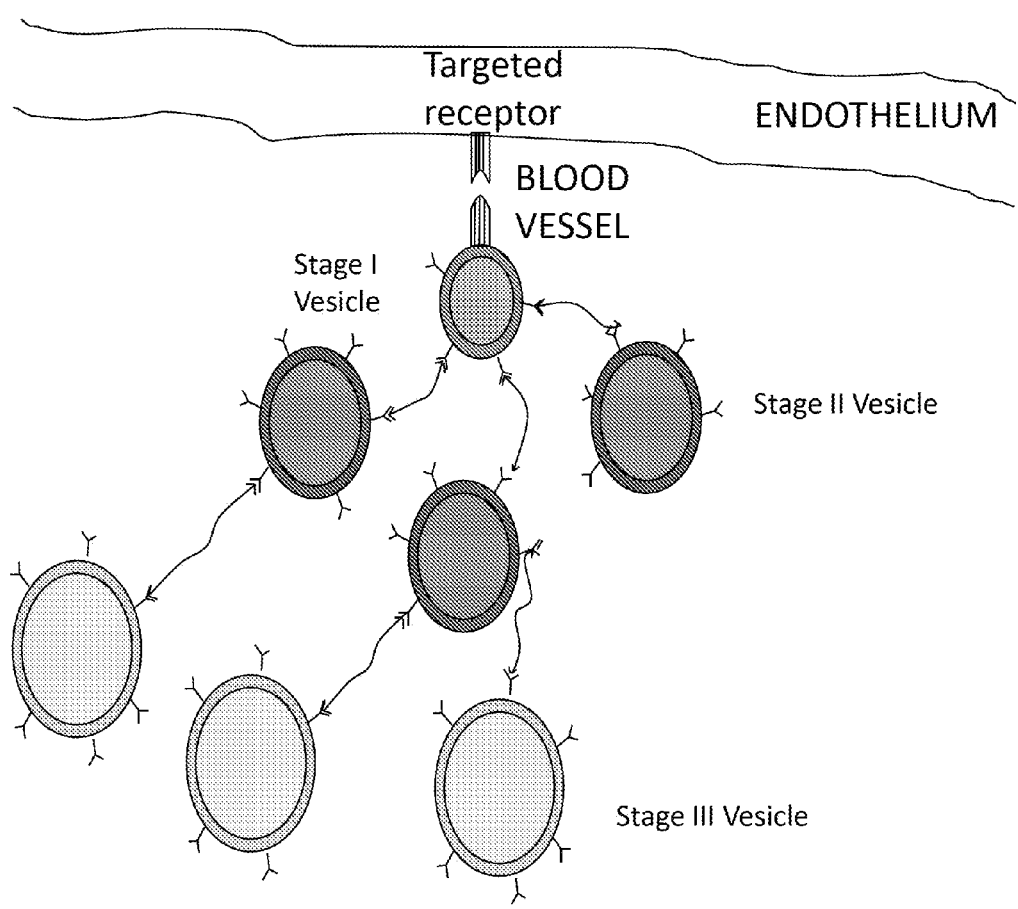
FIG. 2 illustrates the sequentially deliverable combinable formulation of the presently disclosed and claimed inventive concept(s).

The presently disclosed and claimed inventive concept(s) provides a universal multi-modal targeting and therapeutic system that overcomes limitations in the quantity of targeted material through amplification (see FIGS. 1 and 2). The presently disclosed and claimed system has both imaging and therapeutic applications. The therapeutic arm of this system enables new applications that deliver substantially more therapeutics (such as but not limited to, energy, drugs and/or genes) to a targeted site. Particular examples include, but are not limited to, sonoporation and the blood brain barrier; inflammation (i.e., Crohn's disease); targeted and directed chemotherapy; heat increased activity of various therapeutic compositions; targeted and directed ablation; and the like.

As depicted in FIGS. 1 and 2, the presently disclosed and claimed inventive concept(s) is related to a complex of sequentially deliverable pharmaceutical reagents useful for detecting a target exposed in a lumen through imaging, wherein the complex is formed in the lumen. Said complex comprises at least one targeting agent (also referred to herein as a "Stage I agent" or "Stage I vesicle") that binds to a target (Stage I binding), a plurality of amplification agents (also referred to herein as a "Stage II agent" or "Stage II vesicle") and a plurality of imaging agents (also referred to herein as a "Stage III agent" or "Stage III vesicle"). Each of the plurality of amplification agents binds to at least one targeting agent (Stage II binding), and each of the plurality of imaging agents binds to at least one amplification agent (Stage III binding). In addition, at least one of the Stage I, II and/or III agent(s) is detectable by an imaging modality, thus allowing detection of the complex bound to the target.

The Stage I, II and/or III agents may comprise a gas for detection and/or manipulation via ultrasound. In addition, the targeting, amplification and/or imaging agent may contain material that can be detected by imaging modalities other than ultrasound. Yet further in addition, the targeting, amplification and/or imaging agent may further comprise a therapeutic composition incorporated/encapsulated therein. The therapeutic composition may be delivered, used, released, activated and/or excited upon targeting via the Stage I (targeting) agent, as described in more detail herein below. Said release/activation/excitation may be in response to exposure to heat/ultrasound.

The term "therapeutic composition" as utilized herein will be understood to include any composition that exerts a biological effect and thus possesses the ability to modify the physiological system of an organism. The "therapeutic composition" may be biologically active through its own functionalities, or said composition may be biologically active based on its ability to activate or inhibit molecules having their own biological activity. Examples of therapeutic compositions that may be utilized in accordance with the presently disclosed and claimed inventive concept(s) include, but are not limited to, drugs, small molecules, nucleic acids (DNA, RNA siRNA, etc.), proteins/peptides, conjugates, polymers, polymer conjugates, glycoproteins, glycoprotein conjugates, gas, energy, and combinations or derivatives thereof.

In certain embodiments, the agents are provided with at least one binding site thereon, whereby each binding site is one of a complimentary pair (for example but not by way of limitation, biotin-avidin, antibody-antigen, receptor-ligand, etc.). The Stage I (targeting) agent may comprise a primary binding site and a secondary binding site, while the Stage II (amplification) agent may comprise at least two binding sites, such as but not limited to, a tertiary binding site and a quaternary binding site. The at least two binding sites of the amplification agent may be the same or different. The Stage III (imaging) agent may comprise at least one binding site, such as but not limited to, a quinary binding site. In this example, the primary binding site of the targeting agent forms a first binding complex with the target, the secondary binding site of a targeting agent forms a second binding complex with the tertiary binding site of an amplification agent, and the quaternary binding site of an amplification agent forms a third binding complex with the quinary binding site of the imaging agent. In one alternative, the tertiary and quaternary binding sites of the amplification agent are identical and are complementary to the secondary binding site of the targeting agent and the quinary binding site of the imaging agent. In another alternative, the secondary binding site of the targeting agent is identical to the quaternary binding site of the amplification agent, whereby the secondary binding site of the targeting agent can also bind the quinary binding site of an imaging agent to form the third binding complex.

The Stage I (targeting) agent comprises a targeting ligand unique to the target/disease state; however, the amplification and imaging agents (i.e., Stage II and III agents) may be universal. That is, the content of the agent and the linkers/binding sites thereon of the Stage II and III agents may be identical for a given imaging modality and independent of target/disease state. The Stage II and III agents may link with the same complementary pairs independent of the imaging modality utilized. In addition, the Stage II and/or III agents may be multi-modal and thus contain components related to multiple imaging modalities (i.e., combinations of ultrasound, MRI, CR, etc. reagents).

In another alternative, multiple imaging agents may be utilized. In this instance, the Stage II agent may be provided with binding sites for two or more Stage III agents; these binding sites may be a single binding site that binds both Stage III agents, or multiple different binding sites may be provided, based on the number of different Stage III agents to be utilized.

Stage I, II and/or III agents are defined only by the linkers required for a given stage and are independent of their content (see FIG. 2). Stated in another way, the technology is akin to tinker toys comprising hubs and pegs. The pegs (i.e. linkers) define the stage; the hubs can contain anything.

The binding sites described herein above may be any biomolecule that has binding affinity for another substance and is capable of forming a complex therewith, thereby providing affinity between two agents/vesicles. For example but not by way of limitation, the binding sites may be peptides, proteins, antigens, antibodies, antibody fragments, receptors, ligands, glycoconjugates, and combinations or derivatives thereof.

Particular examples of target sites that may be utilized in accordance with the presently disclosed and claimed inventive concept(s) include, but are not limited to, ICAM-1, P-selectin, MadCAM-1, VCAM-1 (i.e., targets for inflammation); $\alpha v\beta 3$ Integrin and VEGFR2 (known in art as targets for angiogenesis); and GP IIb/IIIa (known in art as target for thrombus). A list of exemplary antibodies that may be used as the primary binding site can be found in the following reference: Paul Carter, Nature Reviews Cancer, Vol. 1, pp. 118-129 (November 2001); the entire contents of which are hereby expressly incorporated herein by reference.

In another embodiment, the presently disclosed and claimed inventive concept(s) is directed to a complex of sequentially deliverable pharmaceutical reagents useful for detecting a target exposed in a lumen through imaging, wherein the complex is formed in the lumen. The complex includes at least one Stage I (targeting) agent having a plurality of Stage II (amplification) agents attached thereto, wherein the at least one Stage I (targeting) agent binds to a target exposed in a lumen. Said complex may further comprise a plurality of Stage III agents, wherein each of the plurality of Stage III agents comprises at least one binding site exposed on a surface thereof for binding to a Stage II agent. The at least one binding site on the Stage III agents may also be capable of binding to the at least one Stage I (targeting) agent.

The presently disclosed and claimed inventive concept(s) is also directed to a sequentially deliverable combinable formulation. Said formulation comprises a first administrable composition comprising a Stage I (targeting) agent that is capable of binding to a target exposed in a lumen, a second administrable composition comprising a Stage II (amplification) agent, and a third administrable composition comprising a Stage III (imaging) agent. The Stage II agent comprises a first moiety having affinity for the Stage I agent and a second moiety having affinity for the Stage III agent. The Stage I, II and/or III agent(s) is detectable by an imaging modality, thus allowing amplification of the targeting agent signal bound to the target. The moieties comprise the binding sites described herein previously.

The presently disclosed and claimed inventive concept(s) is further directed to a method of generating enhanced images of a subject's body. Said method comprises the steps of administering to the subject's body the sequentially deliverable combinable formulation described herein above, and generating an ultrasound, magnetic resonance, X-ray or radiographic image of at least a part of said body.

In any of the methods described herein before or herein after, the sequentially deliverable combinable formulation may be administered as follows: first, administering to said body the first administrable composition, and thereafter administering to said body the second administrable composition, and thereafter administering to said body the third administrable composition. In certain embodiments, following administration of the first administrable composition, the body is incubated for an amount of time to allow for binding of the Stage I (targeting) agent to the target exposed in a lumen and substantial clearance of unbound Stage I agent from the lumen. Then following administration of the second administrable composition, the body is incubated for an amount of time to allow for binding of the Stage II (amplification) agent to the Stage I agent and substantial clearance of unbound Stage II agent from the lumen. In addition, following administration of the third administrable composition, the body is incubated for an amount of time to allow for binding of the Stage III agent and substantial clearance of unbound Stage III agent from the lumen. Additional administration(s) of the first, second and/or third administrable compositions may also be included in the method.

Through the use of the phrases "substantial clearance", "substantially clear out" and "substantially wash out", it will be understood that it is not necessary to remove all of one agent from a lumen/bloodstream prior to administration of a second agent. Rather, these phrases simply indicate that a sufficient number of the first agents have been cleared/washed out of the lumen/bloodstream so that sufficient contrast can be seen and a sufficient signal-to-noise ratio is provided.

The presently disclosed and claimed inventive concept(s) is further directed to a kit useful for imaging a target in a lumen. Said kit may include the sequentially deliverable combinable formulation described herein above. In addition, the kit may further include a software module that analyzes information generated by an image delivery device that detects the Stage III agent.

The presently disclosed and claimed inventive concept(s) is further directed to a device for detecting a signal generated by a Stage III (imaging) agent bound to a target in a lumen. The device may include a computing system and an image delivery device that detects Stage III agents. The computing system comprises an application module and a processing unit; the application module comprises a software module that analyzes information generated by an image delivery device, and the processing unit is configured to execute the software module. The Stage III agents detected by the image delivery device are complexed with at least one Stage I (targeting) agent bound to a target and a plurality of Stage II agents bound to the Stage I (targeting) agent. In certain embodiments, the image delivery device may also function as an energy delivery device that delivers directed energy to the target in the lumen to which the complex of Stage I/II/III agent is bound. In particular embodiments, the image/energy delivery device may be an ultrasound image/energy delivery device. The energy delivery device may also serve as a source of acoustic radiation force.

The presently disclosed and claimed inventive concept(s) is also directed to a method of increasing the strength of a signal detected by an imaging modality. The method comprises administering an effective amount of a Stage I (targeting) agent to a subject, wherein the Stage agent travels through the system of the subject and binds to a target exposed on a surface of a lumen (i.e., a luminal wall) of the subject. Next, an effective amount of a Stage II (amplification) agent is administered to the subject, wherein a plurality of Stage II agents bind to the Stage I agent bound to the target. Then, an effective amount of a Stage III agent is administered to the subject, wherein the Stage III agent binds to the Stage II agent bound to the target site via the Stage I agent. Then, a signal produced by the Stage III agent is detected via the imaging modality.

In certain embodiments of the methods described herein above and herein below, it may be desired that following administration of an agent (i.e., targeting/amplification/imaging/therapeutic agents), the method includes a step of allowing non-bound agents to substantially clear out of the lumen (i.e., blood stream) before administration of a subsequent agent.

The presently disclosed and claimed inventive concept(s) is further directed to a method of diagnosing a condition/disorder in a subject. In the method, an effective amount of the Stage I (targeting) agent described herein above is administered to a subject; the Stage I agent comprises a binding site that binds to a target specific to the condition/disorder, and the Stage I agent travels through the system of the subject and binds to any target exposed on a surface of a lumen of the subject. Then, an effective amount of the Stage II (amplification) agent described herein above is administered to the subject, wherein a plurality of Stage II agents bind to the Stage I agent bound to the target site. Then, an effective amount of the Stage III (imaging) agent described herein above is administered to the subject, wherein the Stage III agent binds to the Stage II agent bound to the target site via the Stage I agent. Then, any signal produced by the Stage I, II and/or III agent(s) is detected via one or more imaging modalities, and it is determined that the subject has the condition/disorder if a signal is detected.

The presently disclosed and claimed inventive concept(s) is further directed to a method of treating a condition/disorder in a subject. In said method, an effective amount of the Stage I agent described herein above is administered to a subject; the Stage I agent comprises a binding site that binds to a target specific to the condition/disorder, and the Stage I agent travels through the system of the subject and binds to any target exposed on a surface of a lumen of the subject. Then, an effective amount of the Stage II agent described herein above is administered to the subject, wherein a plurality of Stage II agents bind to the Stage I agent bound to the target site. Then, an effective amount of a Stage III (therapeutic) agent is administered to the subject, wherein the Stage III agent binds to the Stage II agent bound to the target site via the Stage I agent. At least one of the Stage I, II and III agents includes a therapeutic agent that may be effective in treating the condition/disorder. Once the complex is formed, said therapeutic agent present in the Stage I, II and/or III agents may be effective in treating the condition/disorder. Alternatively, the therapeutic agent may be activated following binding to the target site, whereby the activated therapeutic agent is effective in treating the condition/disorder.

The presently disclosed and claimed inventive concept(s) is further directed to a method of delivering a therapeutic composition to a target site. In said method, an effective amount of the Stage I agent described herein above is administered to a subject; the Stage I agent comprises a binding site that binds to a target specific to the condition/disorder, and the Stage I agent travels through the system and binds to any target exposed on a surface of a lumen of the subject. Then, an effective amount of the Stage II agent described herein above is administered to the subject, wherein a plurality of Stage II agents bind to the Stage I agent bound to the target site. Then, an effective amount of a Stage III agent is administered to the subject, wherein the Stage III agent binds to the Stage II agent bound to the target site via the Stage III agent. A therapeutic composition is incorporated/encapsulated within at least one of the Stage I, II and III agents. In one embodiment, the therapeutic composition is delivered to the target site once bound to the target site. Alternatively, the method may further include the step of activating the Stage I, II and/or III agent to release said therapeutic composition and thus deliver the composition to the target site.

Examples of therapeutic applications include, but are not limited to, hyperthermia; tissue heating by several degrees (which may increase the activity of drugs and/or increase the amount of blood flow without permanent tissue damage); tissue heating to a higher level that induces permanent tissue damage for a therapeutic benefit; increasing cavitation and/or agent collapse; tissue ablation; sonoporation induction; increasing drug and gene delivery; and the like. Another therapeutic application includes the induction of ischemia/necrosis of vascularized tissue, as described in further detail herein below.

Any of the imaging methods described herein above may further include the step of administering an effective amount of a therapeutic agent to the subject, wherein the therapeutic agent binds to at least one of the Stage II agent and the Stage III agent bound to the target site via the Stage I agent. In addition, any of the imaging methods described herein above may further include the step of administering an effective amount of a second Stage III agent to the subject, wherein the second Stage III agent binds to at least one of the Stage II agent and the Stage III agent bound to the target site via the Stage I agent.

Any of the agents utilized in any of the methods described herein above or herein below may comprise a gas (i.e., echogenic liposomes), and thus acoustic radiation force may be utilized to increase targeting efficiency by pushing one or more types of agent(s) against the interior surface of the lumen. For example but not by way of limitation, when the Stage I agent comprises a gas, the ultrasound exposure pushes the Stage I agent against the luminal wall and increases the likelihood of interaction of the Stage I agent with the target site. Optionally, when the Stage II agent comprises a gas, the ultrasound exposure pushes the Stage II agent against the luminal wall and increases the likelihood of interaction of the Stage II agent with the Stage I agent bound to the target site.

In any of the methods described herein above or herein after, the target site may be exposed on the surface of at least one of blood-brain barrier, ovaries, pancreas, kidneys, liver, cancerous tissues of any of the above and/or tissues supplying same. The target site may be disease specific.

In any of the methods described herein above or herein after, the imaging modality utilized therein may be selected from the group consisting of ultrasound, magnetic resonance imaging (MRI), computerized tomography (CT), dual source CT (perfusion imaging), diffusion tensor imaging (DTI), delayed enhanced imaging, X-ray and fluoroscopy (contrast fluoroscopy) imaging, computerized SPECT, PET or PET-CT imaging, and molecular imaging (radiopharmaceuticals).

While the use of gas disposed in a Stage I, II and/or III agent has been described herein for use with ultrasound, it is to be understood that the presently disclosed and claimed inventive concept(s) also encompass the use of other compositions disposed in the Stage I, II and/or III agents for use with other imaging/therapeutic modalities. For example, but not by way of limitation, a gadolinium chelate derivative (such as but not limited to, gadolinium-diethylene-triamine-pentacetic acid (see for example, Accardo et al., 2009)) may be utilized with MRI modalities, whereas a radionuclide may be utilized with x-ray modalities (i.e., radiotherapy).

In addition, any of the Stage I, II and/or III agents may be a multimodal echogenic liposome—that is, said agent(s) comprise a gas such that said agent(s) is susceptible to acoustic radiation force, and may also comprise a second imaging modality as described herein above (i.e., MRI, CT, DTI, PET, etc.). Thus, another embodiment of the presently disclosed and claimed inventive concept(s) includes the use of a Stage I (targeting) agent that comprises a multimodal echogenic liposome/microbubble/vesicle. Said Stage I agent may be utilized in the presence or absence of amplification.

The presently disclosed and claimed inventive concept(s) is additionally directed to a complex of sequentially deliverable pharmaceutical reagents useful for detecting a target exposed in a lumen through imaging, wherein the complex is formed in the lumen. The complex comprises at least one Stage I agent as described herein above and a plurality of Stage III (imaging) agents as described herein above. Each of the plurality of Stage III agents binds to at least one Stage I agent, and wherein the Stage I and/or III agents are detectable by an imaging modality, thus allowing detection of the complex bound to the target.

The presently disclosed and claimed inventive concept(s) is further directed to a method of targeting a signal visualized by an imaging modality. In said method an effective amount of a Stage I agent is administered to a subject, wherein the Stage I agent travels through the subject and binds to a target site exposed on a lumen of the subject. An effective amount of a Stage III (imaging) agent is then administered to the subject, whereby the Stage III agent binds to the Stage I agent. A signal produced by the Stage I and/or III agent(s) is then detected by the imaging modality.

In any of the methods described herein, the complex formed in the lumen does not substantially obstruct fluid flow (i.e., blow flow) in the lumen. This is achieved by sequential addition of agents, by limiting the size (structural dimensions) of the individual agents utilized in the methods and/or by limiting the amount of Stage II agent utilized so that the dimensions of the complex formed therefrom are limited and thus do not exceed the dimensions of the lumen. For example, the targeting/amplification/imaging agents may be provided with diameters that are sufficiently small whereby the sum of the three diameters does not exceed the diameter of a capillary (i.e., $\leq 10\mu$; Dayton, 2002).

Alternatively, in any of the methods described herein, the complex formed in the lumen may substantially obstruct blood flow at the target site in the lumen of the subject, thereby resulting in ischemia to a targeted portion (i.e., tissue, organ, body part, etc.) of the subject. Therefore, the presently disclosed and claimed inventive concept(s) is further directed to a method of producing ischemia and necrosis of the vascularized tissue at a targeted site in a subject, as described herein above. In said method, the Stage I, II and III agents are administered as described herein above. Then multiple doses of Stage II and/or III agent(s) are administered until the lumen is substantially obstructed at the target site. Therefore, for sequential additions over time, the Stage III agent may also function as an "amplification agent" in obstructing the lumen.

The complex formed in the lumen may include any combination of agents described herein (i.e., targeting and imaging agents; targeting, amplification, and imaging agents; targeting, amplification and therapeutic agents). In addition, when the complex formed in the lumen includes targeting, amplification and imaging agents, a therapeutic agent (i.e., comprising a chemotherapeutic or other cytotoxic substance encapsulated therein) may be further administered to the subject such that the therapeutic agent binds to the imaging agent and delivers the cytotoxic substance to the ischemic, damaged tissue to provide an additional killing mechanism. Optionally, the imaging agent may be removed from the complex prior to administration of the therapeutic agent, whereby the therapeutic agent subsequently administered will bind to the amplification agent and then deliver the cytotoxic substance to the ischemic, damaged tissue to provide an additional killing mechanism.

This same technique of removing a Stage III agent from the complex following imaging, followed by administration of a subsequent agent (such as but not limited to, another imaging agent or a therapeutic agent), may be utilized in any of the methods described herein above or otherwise contemplated herein. In this fashion, the complex formed from the Stage I agent and one or more Stage II agents forms a substructure/scaffold/lattice network upon which multiple uses (such as but not limited to, multiple imaging techniques or a combination of imaging and therapeutic techniques) may be performed. Optionally, the substructure also allows for multiple applications over the course of time. In this manner, the scaffold can be reused as desired.

In a further alternative, it may be desirable to remove both the Stage III agent as well as the Stage II agent(s), leaving only the Stage I agent to form the scaffold that can be reused for multiple uses or multiple applications.

Any of the methods described herein may also include the step of degrading at least a portion of the complex (or all of the complex) after the protocol (imaging and/or therapeutic) is applied. Degradation may involve the use of energy, heat, chemical methods (i.e., reduction of a disulfide bond in unique way), pH change, addition of a competing agent (Ab), and the like. In this manner, one or more of the targeting/amplification/imaging/therapeutic agents can be ruptured (such as but not limited to, by ultrasound) when desired; in addition, all of the agents can be ruptured when the complex is no longer needed. For example but not by way of limitation, if the spacer is a peptide with an amino acid sequence that is cleaved by an enzyme, the spacer will be cleaved and the complex degraded. The enzyme could be attached to one of the vehicles and may require a cofactor or heat for activation.

The Stage I (targeting) agents utilized in accordance with the presently disclosed and claimed inventive concept(s) is manufactured by providing multiple (i.e., at least two) attaching/binding sites or points on a vesicle framework, as described in greater detail herein below. For the Stage I (targeting) agent, a primary binding site for binding to the target is attached to the vesicle framework through a linker, while a secondary binding site for binding to the Stage II agent is attached to the vesicle framework through another linker.

The Stage II (amplification) agents utilized in accordance with the presently disclosed and claimed inventive concept(s) are manufactured by providing multiple points of attachment (i.e., multiple binding sites) on a vesicle framework. The use of multiple points of attachment will enable: (1) multiple points of attachment for multimodal imaging; (2) multiple applications (over the course of time); and/or (3) multiple uses (such as but not limited to, imaging and therapeutic uses). The amplification agents may be provided with tertiary and quaternary binding sites, as described herein above, and may further be provided with additional binding sites to allow interaction with additional imaging/therapeutic agents (i.e., other than the imaging/therapeutic agent that interacts with the quaternary binding site).

In one embodiment, the tertiary and quaternary binding sites may be attached through the use of linkers. The multiple points of attachment on the amplification vesicle are prepared using a mixture of linkers, as described in greater detail herein below. However, it is to be understood that linkers are not required for the attachment of the tertiary and quaternary binding sites to the amplification agent.

The imaging/therapeutic agents utilized in accordance with the presently disclosed and claimed inventive concept(s) is manufactured by providing at least one point of attachment on a vesicle framework. The at least one point of attachment may be attached to the vesicle framework through a linker; however, it is to be understood that linkers are not required for the attachment of the quinary binding site to the imaging/therapeutic agent.

Production of the targeting/amplification/imaging/therapeutic agents utilized in accordance with the presently disclosed and claimed inventive concept(s) may begin by providing microbubbles, liposomes, or other types of vesicles as a framework, and then adding the binding sites (i.e., linkers/complexing agents) thereto. Examples of general vesicle framework that may be utilized for the targeting/amplification/imaging/therapeutic agents are well known in the art for use in imaging/therapeutic applications (said prior art vesicles produced in the absence of targeting and/or the linkers/complexing agents utilized for producing the scaffolding of the claimed complex). Particular examples include, but are not limited to, the following. U.S. Pat. No. 5,123,414, issued Jun. 23, 1992 to Unger, discloses liposomes suitable as ultrasound contrast agents, said agents containing media of various types including gases, gaseous precursors and perfluorocarbons that are activated by pH, temperature and/or pressure. Unger et al. (2004) disclose microbubbles having perfluorocarbon gases entrapped within lipid coatings with both diagnostic and therapeutic applications, including the ability to be cavitated with ultrasound energy for site-specific local delivery of bioactive materials and for treatment of vascular thrombosis; said reference also discloses that the blood-brain barrier (BBB) can be reversibly opened using ultrasound, which also cavitates microbubbles within the cerebral microvasculature for delivery of both low and high molecular weight therapeutics to the brain. The Review Article of Klibanov (2006) discloses the use of microbubble contrast agents for targeted ultrasound imaging and ultrasound-assisted drug-delivery applications by providing targeting ligands on the surface of the microbubbles. Hernot and Klibanov (2008) describe microbubbles in ultrasound-triggered drug and gene delivery, where the microbubbles enhanced ultrasound energy deposition in target tissues and serve as cavitation nuclei for increased intracellular drug delivery. Ferrante et al. (2009) describe a perfluorocarbon-filled phospholipid microbubble contrast agents targeted to the adhesion molecules P-selectin and VCAM-1 by coupling a polyethylene glycol-biotin-streptavidin bridge with mAb MVCAM.A and/or a sialyl Lewisx polymer (PAA-sLex). Liu et al. (2006) disclose encapsulated ultrasound microbubbles that have targeting ligands attached to the surface thereof, and their applications in drug delivery or gene therapy. Suzuki et al. (2007 and 2008) describe bubble liposomes (which are smaller in diameter than conventional microbubbles) that contain perfluoropropane and use thereof in gene therapy and ultrasonic destruction technology. Tinkov et al. (2009) disclose approaches for manufacturing and drug-loading microbubbles for use as ultrasound triggered drug carriers. Jong et al. (2009) describe different strategies for characterizing ultrasound contrast agents (UCAs), including acoustic and optical methods. Schroeder et al. (2009) describe the interaction of ultrasound with liposomes and the mechanical mechanism of drug release from liposomes using low frequency ultrasound (LFUS), including the effects of liposome lipid composition and physicochemical properties as well as LFUS parameters on liposomal drug release, and the use of acoustic cavitation. Huang (2008) discloses ultrasound-controlled drug release and ultrasound-enhanced drug delivery via liposomes having gas and/or drugs entrapped therein. The entire contents of each of the above-referenced patents and publications are hereby expressly incorporated herein by reference.

In addition, commercially available ultrasound contrast agents that may be utilized in accordance with the presently disclosed and claimed inventive concept(s) include, but are not limited to, SONAZOID™ (GE Healthcare, Oslo, Norway)—see Otani et al. (2009) for disclosure of attaching antibodies thereto; DEFINITY® (Bristol-Myers Squibb Medical Imaging, Billerica, Mass.); and OPTISON™ (GE Healthcare, Oslo, Norway). In addition, various ultrasound contrast agents that may be utilized in accordance with the presently disclosed and claimed inventive concept(s) are produced by Targeson, Inc. (San Diego, Calif.), including but not limited to, TARGESTAR-B®, a biotinylated microbubble contrast agent for conjugation of biotinylated ligands.

Once the vesicle framework is provided, the method of manufacture proceeds by attaching the binding sites thereto; the binding sites may be attached via the use of linkers. Each of the linkers comprises one member of a complementary pair of complexing agents. In Stage I agent/Stage II agent binding, the Stage I (targeting) agent comprises a first member of the complementary pair (i.e., secondary binding site), while the Stage II (amplification) agent comprises a second member of said complementary pair (i.e., tertiary binding site). In amplification agent/imaging (or therapeutic) agent binding, the amplification agent comprises a first member of another complementary pair (i.e., quaternary binding site) while the imaging (or therapeutic) agent comprises a second member of said complementary pair (quinary binding site).

The linkers utilized in accordance with the presently disclosed and claimed inventive concept(s) are provided with functionalization at two terminals. When the two terminals are activated with the same reactive moiety, the linker is referred to as "homobifunctional", whereas if the functional groups present are different, the linker is referred as "heterobifunctional". One of the two terminals attaches the linker to the vesicle framework, while the other terminal comprises the one member of a complementary pair of complexing agents. When utilizing a homobifunctional linker, the same type of connector is utilized at both ends of the linker, and thus connects the linker to the vesicle framework of the agent as well as interacts with the other member of the complementary pair of complexing agents to bind the targeting/amplification/imaging/therapeutic agent to another targeting/amplification/imaging/therapeutic agent. A non-limiting example of a homobifunctional linker is the Avidin-PEG-Avidin (which is readily made and/or commercially available). Many of the linkers potentially exhibit multiple binding sites. Undigested antibodies are bidentate; avidin, streptavidin and neutravidin each offer up to four binding sites. The multidentate molecules can be used in lieu of the homobifunctional linker.

When utilizing a heterobifunctional linker, a first type of connector is utilized for connecting the linker to the vesicle framework of the agent, and a second, different type of connector is utilized for interacting with the target site and/or the other member of the complementary pair of complexing agents to bind the targeting/amplification/imaging/therapeutic agent to another targeting/amplification/imaging/therapeutic agent. A non-limiting example of a heterobifunctional linker is Avidin-PEG-Antibody. The targeting/amplification/imaging/therapeutic agents may be prepared by mixing the appropriate proportions of homo and heterobifunctional linking agents in which both linking agents share a common connector type, wherein this common connector type is the complementary pair of the linker attached to the base vesicle. The mixture is then added to the base vesicle to obtain the desired multiple attaching points.

The linkers may further comprise a tether or extender molecule, such as but not limited to, a peptide or PEG. The size of the individual agents should be sufficient for maximum tethering of two agents via the linkers. The tether/linker should be of sufficient length to maximize binding of agents but not so long that significant entanglement of the tethers/linkers occurs.

In the production of the Stage I (targeting) agent, a heterobifunctional linker is utilized to attach the primary binding site to the Stage I agent. For example but not by way of limitation, an avidinylated liposome/microbubble (which is readily made and/or commercially available) may be provided and interacted with Biotin-PEG-Antibody, wherein the antibody may be any antibody that is commercially available or otherwise known in the art. The precursor of avidinylated vesicle framework-Biotin-PEG- provides a universal precursor that may be utilized with any binding molecule to form any desired Stage I agent. For example, said precursor may be provided, and then different antibodies for different types of disorders/diseases/cancers may be attached thereto. In addition, multiple antibodies/binding molecules may be utilized for the primary binding site.

A heterobifunctional or homobifunctional linker may then be used to attach the secondary binding site (for binding to the amplification agent) to the vesicle framework. For example but not by way of limitation, the homobifunctional linker Biotin-PEG-Biotin may be utilized, wherein the Biotin forms the secondary binding site and can thus interact with an amplification agent that comprises a biotinylated liposome/microbubble having an Avidin-PEG-Avidin linker attached thereto (i.e., the Avidin forms the tertiary binding site that interacts with the Biotin secondary binding site).

In the production of the Stage II (amplification) agent, the tertiary and quaternary binding sites may be attached to the vesicle framework by any method known in the art. For example, the Stage II agent may simply comprise a biotinylated microbubble, wherein the biotin on the Stage II agent comprises the tertiary and quaternary binding sites and interacts with avidin as the secondary and quinary binding sites. Moreover, the Stage II agent may comprise additional binding sites attached to the vesicle framework, wherein said additional binding sites render the vesicle multifunctional and thus allow for multimodal imaging, multiple applications and/or multiple uses (imaging and/or therapeutic).

In an alternative method of producing the Stage II agent, a homobifunctional or heterobifunctional linker may be utilized to attach the tertiary binding site to the vesicle framework, and at least one additional heterobifunctional linker may be utilized to attach the quaternary binding site to the vesicle framework. Moreover, the Stage II agent may comprise additional binding sites attached to the vesicle framework via heterobifunctional linkers. These additional binding sites render the vesicle multifunctional and thus allow for multimodal imaging, multiple applications and/or multiple uses (imaging and/or therapeutic). For example but not by way of limitation, the Stage II agent may comprise a biotinylated liposome/microbubble having an Avidin-PEG-Avidin homobifunctional linker attached thereto for forming the tertiary binding site (that interacts with the Biotin secondary binding site of the Stage I agent), and further comprises a heterobifunctional linker, such as but not limited to, Avidin-PEG-Biotin, wherein the Biotin forms the quaternary binding site that interacts with the quinary binding site of the Stage III agent. In addition, any free Avidin-PEG-Avidin linkers attached to the Stage II agent that do not bind to the Stage I agent may further be utilized as an additional binding site for capturing a second imaging/therapeutic agent.

In the production of the Stage III agent, the quinary binding site may be attached to the vesicle framework by any method known in the art. For example but not by way of limitation, the Stage III agent may simply comprise a biotinylated microbubble, wherein the biotin (i.e., quinary binding site) on the Stage III agent interacts with avidin (i.e., quaternary binding site) attached to the Stage II agent.

In an alternative method for producing the Stage III agent, a homobifunctional or heterobifunctional linker may be utilized to attach the quinary binding site to the vesicle framework. For example but not by way of limitation, a homobifunctional linker Avidin-PEG-Avidin may be utilized, wherein the Avidin forms the quinary binding site and can thus interact with Stage II agent that comprises a biotinylated liposome/microbubble (i.e., the biotin forms the quaternary binding site that interacts with the Avidin quinary binding site).

In addition, the Stage III agent may further comprise additional binding sites attached to the vesicle framework. These additional binding sites may function to allow additional agents to bind thereto (i.e., another imaging agent or a therapeutic agent). For example but not by way of limitation, a first imaging agent (an ultrasound contrast agent) may comprise an additional binding site of an anti-fluorescein antibody attached thereto. This first imaging agent may be utilized with a second imaging agent for MRI detection, wherein the second imaging agent is provided with fluorescein on a surface thereof. These additional binding sites may be attached by any method known in the art including, but not limited to, via heterobifunctional linkers.

EXAMPLES

Examples are provided hereinbelow. However, the present invention is to be understood to not be limited in its application to the specific experimentation, results and laboratory procedures. Rather, the Examples are simply provided as one of various embodiments and are meant to be exemplary, not exhaustive.

Example 1

In Vitro Formation of the Stage I Agent/Stage II Agent/Stage III Agent Complex In this Example, the proposed in vitro agent critical raw materials (CRMs) were fluoresceinated BSA and 2H1 (an antibody to fluorescein). A polystyrene binding surface was prepared by fluoresceinating BSA, and then binding the fluoresceinated BSA to polystyrene (pH 8, bicarb buffer). The fluoresceinated BSA served as the target for the primary binding site of the Stage I (targeting) agent.

Preparation of Stage I (targeting) agent: Commercially available biotinylated microbubbles (i.e., targeting agent, Targestar B, obtained from Targeson, Inc., San Diego, Calif.) and 2H1 antibody (which binds to fluoresceinated BSA) were obtained. Avidin-PEG-2H1 (i.e., the primary binding site on the targeting agent) was prepared from heterobifunctional PEG, while Avidin-PEG-Avidin (i.e., the secondary binding site on the targeting agent) was prepared from homobifunctional PEG. The Avidin-PEG-2H1 and Avidin-PEG-Avidin were reacted with the biotinylated microbubbles to form the primary and secondary binding sites of the Stage I (targeting) agent, respectively.

Preparation of Stage II (amplification) agent: Commercially available biotinylated microbubbles functioned as Stage II agent in this Example. The biotinylation sites function as both the tertiary and quaternary binding sites of the Stage II agent.

Preparation of Stage III (imaging) agent: Commercially available biotinylated microbubbles were provided and reacted with Avidin-PEG-Avidin to form the quinary binding site of the Stage III agent.

Formation of the Stage I (targeting) agent/target complex: The Stage I (targeting) agent was reacted with the polystyrene binding surface, and the Avidin-PEG-2H1 on the targeting microbubbles bound to the fluoresceinated BSA on the polystyrene binding surface. The polystyrene binding surface was then washed to remove any unbound microbubbles. If desired, binding and ultrasound effects were measured at this time.

Formation of amplification complex: The Stage II (amplification) agent was reacted with the polystyrene binding surface having the Stage I (targeting) agent bound thereto, and the biotinylation site (i.e., the tertiary binding site) on the Stage II (amplification) agent interacted with the Avidin-PEG-Avidin (i.e., secondary binding site) on the Stage I (targeting) agent, whereby the Stage II (amplification) agent bound to the Stage I (targeting) agent bound to the polystyrene binding surface. The binding surface was then washed to remove any unbound biotinylated microbubbles (i.e., Stage II (amplification) agents). If desired, binding and ultrasound effects were measured at this time.

Formation of imaging complex: The Stage III agent was reacted with the polystyrene binding surface having the Stage I/II agents bound thereto, and the Avidin (i.e., quinary binding site) on the Stage III agent interacted with the biotinylation site (i.e., quaternary binding site) on the Stage II (amplification) agent. Thus, the Stage III agent bound to the Stage II (amplification) agent bound to the Stage I (targeting) agent bound to the polystyrene binding surface. The binding surface was then washed to remove any unbound microbubbles (i.e., imaging agents).

Binding and ultrasound effects were measured at this time, to confirm the enhancement of ultrasound contrast agent signal (CPS), and also to verify the bubble heating calculations in vitro to demonstrate that bubble aggregation was not affected.

In addition, bubble aggregation was studied with optical microscopy to confirm the three stages of binding.

Example 2

In Vivo Ultrasound Use of Targeting/Imaging Agent Complex

Preparation of Targeting Component: First, avidinylated unilaminar liposome preparation was prepared according to the procedure described in Szoka and Papahadjopoulos (1978) with the exception that the phospholipids are avidinylated. Biotin—$PEG_{30}$—Antibody was prepared from heterobifunctional crosslinker obtained from Thermo-Fisher. The antibody in this instance may be taken from the list found in Nature Reviews Cancer, Vol. 1, pp. 118-129 (November 2001). Biotin—$PEG_{30}$—Biotin was prepared from homobifunctional crosslinker obtained from Thermo-Fisher. The Biotin—$PEG_{30}$—Biotin and the Biotin—$PEG_{30}$—Antibody were mixed with the avidinylated unilaminar liposomes to prepare targeting reagent.

Preparation of Imaging Component: Commercially available biotinylated microbubbles were used. Avidin—$PEG_{30}$—Avidin was prepared from homobifunctional crosslinker obtained from Thermo-Fisher. The biotinylated microbubbles were mixed with Avidin—$PEG_{30}$—Avidin to obtain the imaging component.

In the method of use, the targeting component/liposome preparation is injected into the bloodstream, and the patient is incubated with said component for a sufficient amount of time (such as but not limited to, about 3-10 minutes) so that targeting occurs and circulating free liposomes substantially wash out of the bloodstream. Next, the patient is injected with an effective amount of the imaging component, and the patient is incubated with said component for a sufficient amount of time (such as but not limited to, about 3-10 minutes) so that secondary targeting occurs and circulating free microbubbles substantially wash out of the bloodstream. Diagnostic imaging of targeted agent or targeted therapeutic activity is then performed.

Example 3

In Vivo Ultrasound Use of Targeting/Amplification/Imaging Agent Complex

Preparation of Targeting Component: First, biotinylated unilaminar liposome preparation was prepared according to the procedure described in Szoka and Papahadjopoulos (1978). Avidin—$PEG_{30}$—Antibody was prepared from heterobifunctional crosslinker obtained from Thermo-Fisher. The antibody in this instance may be taken from the list found in Nature Reviews Cancer, Vol. 1, pp. 118-129 (November 2001). Avidin—$PEG_{30}$—Avidin was prepared from homobifunctional crosslinker obtained from Thermo-Fisher. The Avidin—$PEG_{30}$—Avidin and the Avidin—$PEG_{30}$—Antibody were mixed with the biotinylated unilaminar liposomes to prepare targeting reagent.

Preparation of Amplification Component: Biotinylated unilaminar liposome preparation was prepared according to procedure described in Szoka and Papahadjopoulos (1978).

Preparation of Ultrasound Imaging Component: Commercially available streptavidin ultrasound imaging agent (Targestar SA from Targeson, Inc., San Diego, Calif.) was used.

In the method of use, the targeting component/liposome preparation is injected into the bloodstream, and the patient is incubated with said component for a sufficient amount of time (such as but not limited to, about 3-10 minutes) so that targeting occurs and circulating free liposomes substantially wash out of the bloodstream. Next, the patient is injected with an effective amount of the amplification component, and the patient is incubated with said component for a sufficient amount of time (such as but not limited to, about 3-10 minutes) so that secondary targeting occurs and circulating free vesicles substantially wash out of the bloodstream. Next, the patient is injected with an effective amount of the imaging component, and the patient is incubated with said component for a sufficient amount of time (such as but not limited to, about 3-10 minutes) so that secondary targeting occurs and circulating free vesicles substantially wash out of the bloodstream. Diagnostic imaging of targeted agent or targeted therapeutic activity is then performed.

Example 4

In Vivo MRI Use of Targeting/Amplification/Imaging Agent Complex

This Example proceeds in a similar fashion to Example 3, except that an MR imaging component is substituted for the ultrasound imaging component. The MR Imaging Component is prepared as follows: Contrast agents are entrapped within the internal aqueous space of the biotinylated liposomes; the contrast agent should have high molecular weight to enhance signal. Examples of contrast agents include, but are not limited to, macromolecular gadolinium(III) chelates such as dendrimers, linear polymers, gadofullurenes, gadonanotubes, and large proteins (see for example, Accardo et al., 2009).

Lipophilic contrast agents are incorporated in the lipid bilayer of the multilaminar liposome. Avidin—$PEG_{30}$—Avidin is prepared from homobifunctional crosslinker obtained from Thermo-Fisher. The biotinylated liposomes are mixed with Avidin—$PEG_{30}$—Avidin to obtain the MR imaging component.

Gd-DTPA is a common MRI contrast agent. A typical dose is 0.17 mmol/kg body weight. The molecule has a molecular weight of 0.56 kDa and a diameter of 10.0 Å (Higgins et al., 2006).

$0.17 \times 10^{-3}$ moles/kg×100 kg/body×$6.022 \times 10^{23}$ molecules/mole=$1.02 \times 10^{23}$ molecules/body Assuming 6 liters of blood per body, there would be $1.7 \times 10^{15}$ particles per µL of blood in a regular dose of agent. Blood forms about 10% (between 5-14% depending on tissue type) of the volume of a given region of tissue, so there are about $1.7 \times 10^{14}$ particles in a µL of tissue.

Surface loading of contrast molecule: the surface area of a sphere of radius r is given by $4\pi r^2$. A 3 µm diameter sphere has a surface area of $2.8 \times 10^{-11}$ m$^2$. A Gd-DTPA molecule has a cross sectional area of $7.85 \times 10^{-19}$ m$^2$. Therefore, about $36 \times 10^6$ Gd-DTPA particles will fit around the surface of each sphere.

Assuming there are 100 spheres in a 1 µL of targeted region, this will provide $3.6 \times 10^9$ Gd-DTPA particles targeted with full particle packing around each sphere. This is about 0.002% of the regular dose.

However, in some work at the University of Wisconsin, antibodies capable of binding 100 Gd ions per molecule were created (Glazer et al., 2004). This work cited antibody concentrations as low as 0.1 µM as sufficient for imaging in vivo.

$0.1 \times 10^{-6}$ moles/liter×$10^{-6}$ liter/uL×$6.022 \times 10^{23}$ molecules/mole=$60.2 \times 10^9$ antibodies/µL→$6.02 \times 10^{12}$ Gd ions/µL According to this work, about $6 \times 10^{12}$ Gd complexes in a 4 should achieve an image with MRI. This requires an amplification factor of over 1600 over the assumed 100 sphere full particle packing case.

Therefore, the present Example utilizing MRI agents with better contrast to provide greater numbers of Gd-DTPA particles targeted to the targeted spheres. In one embodiment, PEG chains provide additional binding sites that could greatly increase the number of Gd-DTPA particles that are bound to each sphere.

Volume loading of contrast molecule: The volume or a sphere if radius r is given by $4/3\pi r^3$. A 3 μm diameter sphere has a volume of $1.4 \times 10^{-12}$ m$^3$. A Gd-DTPA molecule has a volume of about $5.28 \times 10^{-28}$ m$^3$. Therefore, about $26 \times 10^9$ Gd-DTPA particles should fit within the volume of each sphere. The molecules are suspended or somehow constrained so that the MRI response is maximized.

By targeting 10 spheres per 4, about $260 \times 10^9$ Gd complexes per 4 will be achieved, which is about factor of 23 less than the required to image with MRI ($6 \times 10^{12}$ complexes per 4). The MRI detectability limit can be achieved with an amplification factor of 23. Greater levels of amplification may relax the requirement on the number of Gd-DTPA particles that must be loaded onto the spheres.

Increasing the volume of the targeting spheres to be able to load more Gd complexes will also help. A 10% increase in diameter will yield a 30% increase in Gd payload capacity.

Conclusions: Amplification will enable targeted MRI contrast imaging by increasing the number of Gd complexes delivered to a region to a level sufficient to be detected. Amplified targeted MRI contrast agents are confined to the vascular lumen.

Example 5

Method of Delivering Heat to a Localized Site in the Body to Treat a Disease State/Ailment/Cancer A set of liposomes coated with antibodies that target the localized site in the body are provided. The set of liposomes is also coated with one member of a complementary pair of complexing agents.

A set of microbubbles is provided, wherein the set of microbubbles is coated with the other member of the complementary pair of complexing agents. Each of the set of microbubbles is filled with gas.

The patient is injected with an effective amount of the set of liposomes, and the patient is incubated with the liposomes for a sufficient amount of time (such as but not limited to, about 3-10 minutes) so that targeting occurs and circulating free liposomes substantially wash out of the bloodstream. Next, the patient is injected with an effective amount of the set of microbubbles, and the patient is incubated with said set of microbubbles for a sufficient amount of time (such as but not limited to, about 3-10 minutes) so that secondary targeting (i.e., amplification) occurs and circulating free microbubbles substantially wash out of the bloodstream.

Ultrasound is then applied to a localized portion of the patient, whereby the ultrasound is applied at the appropriate frequency and amplitude such that the sound energy is absorbed by the material and is converted to heat. In this manner, the localized tissue is heated to a point where necrosis occurs with minimal damage to surrounding tissue.

In this method, the bubble size is selected to maximize the absorption of sound without blocking flow of blood.

Example 6

In Vivo Therapeutic Use of Targeting/Imaging Agent Complex

The targeting component is prepared as in Example 2.
Preparation of Therapeutic Component for use in US and PET applications: Commercially available biotinylated microbubbles are used for ultrasound applications. Commercially available biotinylated radiopharmaceuticals are used for PET applications. Avidin—PEG$_{30}$—Avidin is prepared from homobifunctional crosslinker obtained from Thermo-Fisher. The biotinylated microbubbles are mixed with Avidin—PEG$_{30}$—Avidin to obtain the therapeutic component.

In the method of use, the targeting component/liposome preparation is injected into the bloodstream, and the patient is incubated with said component for a sufficient amount of time (such as but not limited to, about 3-10 minutes) so that targeting occurs and circulating free liposomes substantially wash out of the bloodstream. Next, the patient is injected with an effective amount of the imaging component, and the patient is incubated with said component for a sufficient amount of time (such as but not limited to, about 3-10 minutes) so that secondary targeting occurs and circulating free microbubbles substantially wash out of the bloodstream. Secondary target free bubble activity can be monitored with imaging modality. Diagnostic imaging of targeted agent and/or targeted therapeutic activity is then performed.

Some common PET tracer isotopes are $^{11}$C, $^{13}$N, $^{15}$O, $^{18}$F, $^{64}$Cu, $^{62}$Cu, $^{124}$I, $^{76}$Br, $^{82}$Rb and $^{68}$Ga, with $^{18}$F. The typical sensitivity of a PET scanner allows detection of between $10^{-11}$ and $10^{-12}$ mol/L concentrations. This Example also expects resolution on the order of several millimeters.

$10^{-11}$ moles/L×$6.022\times10^{23}$ molecules/mole×$10^{-6}$ L/μL=$6\times10^6$ molecules/μL Assuming there are 100 targeting spheres in a 1 μL of targeted region, then about 60,000 isotope particles are needed in each targeting sphere.

A unilamellar liposome with a diameter of 100 nm (0.1 μm) composed of a 5 nm thick bilayer of phosphatidylcholine contains $$N_{tot} = 17.69 \times \left[\left(\frac{d}{2}\right)^2 + \left(\frac{d}{2}-5\right)^2\right]$$

molecules or about 80,000. With the same 5 nm bilayer thickness, a 1000 nm (1 μm) liposome contains about 8.8 million molecules.

Therefore, about 60000 isotope particles per $8.8\times10^6$ molecules or a concentration of 0.68% radioactive material are needed, assuming the shell is the only place containing the isotope.

However, isotopic water may also be encapsulated within the volume of a 1 μm shell, thus providing:

$$\frac{4}{3}\pi(0.5\times10^{-6}m)^3 \times \frac{10^6 \text{ mL}}{m^3} \times \frac{1 \text{ g}}{\text{mL}} \times \frac{1 \text{ mole}}{18 \text{ g}} \times 6\times10^{23} \text{ molecules/mole} = 17.5\times10^9 \text{ molecules}$$

The 60,000 isotope particles per $17.5\times10^9$ molecules corresponds to a radioactive isotope concentration of about 3 parts per million in water.

The prior art discloses the labeling of liposome shells rather than the water within. However, the lipid bilayer is permeable to water molecules and impermeable to ions and small hydrophilic molecules like glucose and larger macromolecules like proteins and RNA. So the present Example encompasses the labeling of not only liposome shells but also the water encapsulated therein. The use of larger radioactively tagged molecules in the water encapsulated in the liposome shells is required for labeling to ensure they are maintained within the liposome shell.

Example 7

In Vivo Therapeutic Use of Targeting/Amplification/Therapeutic Agent Complex The targeting component and amplification component are prepared as described in Example 3.

Preparation of Therapeutic Component: Commercially available biotinylated microbubbles are used for ultrasound applications (note that the imaging agent and therapeutic agent may be the same agent). Commercially available biotinylated radiopharmaceuticals are used for PET applications. Avidin—$PEG_{30}$—Avidin is prepared from homobifunctional crosslinker obtained from Thermo-Fisher. The biotinylated microbubbles are mixed with Avidin—$PEG_{30}$—Avidin to obtain the therapeutic component.

In the method of use, the targeting component/liposome preparation is injected into the bloodstream, and the patient is incubated with said component for a sufficient amount of time (such as but not limited to, about 3-10 minutes) so that targeting occurs and circulating free liposomes substantially wash out of the bloodstream. Next, the patient is injected with an effective amount of the amplification component, and the patient is incubated with said component for a sufficient amount of time (such as but not limited to, about 3-10 minutes) so that secondary targeting occurs and circulating free liposomes substantially wash out of the bloodstream. Next, the patient is injected with an effective amount of the therapeutic component, and the patient is incubated with said component for a sufficient amount of time (such as but not limited to, about 3-10 minutes) so that binding of the therapeutic component to the target/amplification complex occurs and circulating free microbubbles substantially wash out of the bloodstream. Therapeutic component free bubble activity can be monitored with an imaging modality. Diagnostic imaging of targeted agent and/or targeted therapeutic activity is then performed.

Example 8

In Vivo Therapeutic Use of Targeting/Amplification/Imaging Complex to Induce Ischemia This Example proceeds as described in Example 7. Once diagnostic imaging confirms that the complex of Stage I agent/Stage II agent/Stage III agent has formed at the target site, an additional amount of Stage II (amplification) agent and/or Stage III (imaging) agent is administered. While visualizing through imaging, additional amounts of agents with complementary pairs (binding sites) to those exposed on the complex are administered in a sequential fashion until the vessel is substantially obstructed at the target site. Obstruction of the lumen at the target site results in necrosis of the vascularized tissue at the target site. The process of necrosis may be monitored using the appropriate imaging modality, and the obstruction may be eliminated via ultrasound when desired.

Example 9

Calculations Related to the Heating Effects of Bubbles in Tissue

Bubble kinetic energy: Based on Kirk T. McDonald, "Single-Bubble Sonoluminescence", Joseph Henry Laboratories, Princeton University, Princeton, N.J. 08544 (Feb. 2, 1995) (published at www.physics.princeton.edu/~mcdonald/examples/sonobubble.pdf) the maximum kinetic energy available in a collapsing bubble was computed. Assuming the bubble starts out nominally at 3 μm diameter and expands to 10 μm (the maximum that will fit in a capillary) and collapses to 1 μm without popping, the amount of energy available in the size change from 10 μm to 1 μm is given by:

$$W = P\Delta V = \frac{4\pi P}{3}(R_1^3 - R_2^3)$$

Where P is 1 Atm or $10^5$ N/m$^2$ $W=5.2\times10^{-11}$ J kinetic energy available in size change (10 to 1 μm)

Energy available in bubbles per cycle of insonation: Assuming 100% of the kinetic energy from the size change (from both the increasing and decreasing phases) of 10 targeted bubbles in a 1 μL volume could be converted to heat, the amount of energy converted to heat per cycle is given by:

$E_{bubbles}=2\cdot5.2\times10^{-11}\times10=10^{-9}$ J/cycle in a 1 μL volume

Greater amounts of energy could be dissipated with larger number of targeted bubbles. A lesser amount of energy is available if all of the kinetic energy is not converted to heat. Only a fraction of this energy would be converted to heat depending on the bubble damping factor.

Bubble Heat dissipation: From de Jong et al. (2009), for small excitation levels, the displacement of a bubble wall in a liquid environment is characterized by an equation of motion: $m\ddot{x}+\beta\dot{x}+Sx=F_{drive}$, where m is the mass of the bubble-liquid system, β is the mechanical resistance related to the dissipation, S is the stiffness of the system, $F_{drive}(t)$ is the driving force, and x(t) is the radial displacement of the bubble wall relative to the initial radius $R_0$. The equations for mass, mechanical resistance and stiffness are as follows:

$m=4\pi R_0\rho$ where p is the density of the surrounding medium $\beta=\delta_{total}\omega m$ where $\delta_{total}$ is the total damping and ω the angular frequency $S=12\pi\kappa P_0 R_0$ where κ is the heat capacity ratio $C_p/C_v$, and $P_0$ is ambient pressure, The equations for the resonance frequency and Q factor of a second order system characterized by $L(s^2+2\alpha s+\omega_0^2)$, rewritten as $$m\left(s^2 + \frac{\beta}{m}s + \frac{S}{m}\right),$$

is $$\omega_0 = \sqrt{\frac{S}{m}} \text{ and } \alpha = \frac{\beta}{2m} \text{ and } Q = \frac{\omega_0}{\alpha}.$$

Substituting the earlier equation for β, we find $$Q = \frac{2}{\delta_{total}}$$

De Jong et al. suggest a damping coefficient $\delta_{total}$ on the order of 0.1 for gas bubbles in water between 1 and 10 µm diameter, leading to a Q of 20, which leads to a conversion factor of about 5% (1/Q).

In reality, the viscous damping of blood is about three times higher than water, so de Jong et al. (2002) suggest a total damping coefficient closer to 0.5, starting from a damping coefficient in water of 0.15 for bubbles with diameters between 4 µm and 10 µm, which leads to a Q of 4 and a therefore a higher conversion of ultrasound to heat will be seen—on the order of 25%.

A 25% conversion factor was used for the calculations which follow.

Tissue Heating: It is assumed that all attenuation of high frequency sound in tissue is due to absorption and that all of this energy is converted to heat. Assuming an attenuation of 0.4 dB/cm-MHz and a tissue heat capacity, $\rho=3.5$ J/g° C. the power dissipation as a function of insonation frequency assuming that the maximum allowable power of 720 mW/cm² is used is plotted in FIG. 4. It is also assumed that the density of tissue is equal to water, which should be accurate to within about 5%.

The goal of targeted heat therapy is to find a range of insonation frequencies and bubble geometry and composition where heating from bubbles is greater than heating from tissue. Heating from bubble size change kinetic energy transformed to heat will depend on the number of bubbles in a given volume as well as how much of the kinetic energy is transformed to heat from the viscous friction from the bubble shell.

Measurements from the 4C1 abdominal probe on the Siemens Acuson Sequoia ultrasound system were made for a specific imaging condition: 160 mm depth with a 20 mm wide field of view while performing contrast pulse sequencing (CPS) imaging with a 21 dB power reduction from maximum to avoid bubble destruction. The power spatial peak, temporal average, (SPTA) and mechanical index (MI) are shown in Table 1.

TABLE 1

| CPS frequency (MHz) | Reduced power SPTA (mW/cm²) | Reduced power MI | Full power (+21 dB) SPTA | Full Power MI |
|---|---|---|---|---|
| 1.5 | 3.76 | .21 | 434 | 1.9 |
| 2.0 | 2.88 | .21 | 341 | 1.9 |
| 2.5 | 6.46 | .22 | 624 | 1.9 |

In all cases the system transmit about 2 cycles every 267 µsec, spread out over 3 collinear firings and 10 transmit lines at a frame rate of 124 Hz.

For the case of P2.0, or 2.0 MHz transmit, the 2 cycles every 267 µsec repeated 3 times at 124 Hz leads to 744 cycles per second for each line in the field of view. The FDA thermal limit of 720 mW/cm² allows for a 250 fold increase in duty cycle (2.88 mW/cm² to 720 mW/cm²), increasing the number of bubble cycles per second to 186,000. With a maximum ten-bubble kinetic energy of $10^{-9}$ J/sec in 1 µL the total power dissipated, assuming 100% conversion of kinetic energy to heat is 186 µW, as shown in Table 2.

TABLE 2

| Frequency (MHz) | Maximum duty cycle increase possible assuming 2 cycles to start | Maximum power increase possible before 720 mW/cm² FDA limit | Best possible 10 bubble dissipation power transfer assuming 100% conversion |
|---|---|---|---|
| 1.5 | 200 x | 190 x | 141 µW |
| 2.0 | 267 x | 250 x | 186 µW |
| 2.5 | 333 x | 111 x | 82 µW |

The time to increase the tissue temperature by 1° C. for tissue heating due to insonation and to heating due to targeted bubble conversion of sound to heat is plotted in FIG. 5. The heat capacity of the tissue is assumed to be $\rho=3.5$ J/g° C.

Targeted bubble therapeutic effectiveness occurs when the time to increase a given volume of tissue by 1° C. is greater for bubbles than it is for tissue. The actual therapeutic effect would be achieved with a temperature rise of several degrees, taking possibly several minutes to reach the desired temperature.

In the examples shown in FIGS. 4 and 5, increasing the number of bubbles from 10 bubbles per microliter to 100 bubbles per microliter will increase the heating contribution of the bubbles to an amount substantially greater than the heating contribution of the tissue. Depending on the bubble size, insonation frequency, and intensity, a varying number of bubbles is required to achieve the crossover from mainly tissue heating to mainly bubble heating and into a regime of therapeutic benefit.

These curves demonstrate that it is possible to heat regions of targeted agent faster than normal tissue if sufficient aggregated bubbles and a high level of conversion of sound to heat are achieved. Smaller maximum bubble sizes will reduce the power dissipated by bubbles. The power is proportional to the third power of the radius. There are limits on how large the bubbles can be expanded since the water will boil at body temperature at pressures approaching 6 kPa.

It will be possible to further defocus the ultrasonic insonation beams in elevation to maximize the power transfer to bubbles over a volume, staying within the thermal and MI limits mandated by safety considerations Sphere Packing and Bubble Amplification and Aggregation A stage of amplification can increase the number of bubbles that are targeted to a particular region of the tissue by a factor which is proportional to the increase in surface targeting area provided by a targeting liposome.

Consider the following case, where a single targeting liposome is attached to a surface ligand of a capillary blood vessel. For targeting liposomes and bubbles which are all of the same diameter and with ideal packing of spheres bounded by a half-plane (i.e. the capillary wall), up to nine bubbles can be attached to a single targeting liposome, shown in FIG. 6A.

With two stages of amplification a maximum amplification factor of 38 over the single targeting liposome is possible, based on perfect half-plane sphere packing with spheres of identical diameter. A single targeting liposome (Stage I agent, shown in black) has 9 adhering Stage II (amplification) liposomes (shown in grey). For Stage III, twenty eight liposomes form the final adhering cluster, shown in three row levels in the FIG. 6B. The 38 fold amplification is obtained from the nine bound spheres for Stage II and the 28 additional bound spheres for Stage III (along with the one Stage I liposome).

In practice the actual level of amplification may be lower since bubbles are not all of uniform diameter allowing gaps between bubbles and less efficient packing.

Bubbles which are highly clustered may experience smaller changes in diameter in response to insonation pressure change than single free bubbles, potentially somewhat limiting the heat conversion improvements from increased bubble aggregation.

In order to efficiently transfer acoustic energy to targeted bubbles to achieve meaningful therapeutic effect it will be necessary to increase the number of targeted bubbles that attach within a tissue region. The increase in bubble attachment is achievable with the amplification scheme previously described.

Amplification can be combined with other bubble attachment improvements such as acoustic radiation force to further increase targeted bubble aggregation. Acoustic radiation force can be applied to the initial targeting liposome or to any or all of the stages of liposome amplification, including the final gas filled imaging or therapeutic liposome stage.

After thermal treatment, high acoustic pressure pulses (i.e. MI>0.7) can be applied to destroy the aggregated gas filled bubble shells and disperse the bubbles. This can help avoid longer term blockage of capillaries after therapy.

Prior to therapeutic energy delivery, freely circulating bubbles can be destroyed by high intensity, short bursts of acoustic energy directed towards larger blood vessels or the chambers of the heart to ensure that subsequent thermal energy delivery phase is better localized to the treatment targets—the targeted aggregations of bubbles rather than the freely circulating bubbles.

Example 10

Confirmation of Multistage Amplification Utilizing a BIACORE™ X100 Optical Biosensor This Example demonstrates multistage amplification in situ. The protocol for multistage amplification of Example 10 involved four steps. To begin, the target/binding surface was prepared by attaching a fluoresceinated BSA (F-BSA) to a gold surface of a BIACORE™ flow cell. In Stage 1, 2H1-neutravidin was bound to the F-BSA. Then, biotinylated microbubbles were allowed to saturate the surface of the 2H1-neutravidin on the BIACORE™ surface. In Stage 2, neutravidin was allowed to bind to the Stage 1 biotin microbubbles. This was followed by the addition of more biotin microbubbles that were allowed to bind to the Stage 1 neutravidin microbubble complex. In Stage 3, neutravidin was allowed to bind to the Stage 2 microbubbles. Then biotin microbubbles were again allowed to bind to the Stage 2 neutravidin microbubble complex.

FIG. 7a depicts the BIACORE™ dose response curve for Stage 1 binding. In this experiment, the BIACORE™ surface was saturated with binding agent (i.e., neutravidin), and the microbubbles were the limiting reagent. As microbubbles were added, the signal increased in a linear fashion. This observation establishes that the change in signal was directly related to the binding of microbubbles on the BIACORE™ surface.

The Table in FIG. 7b illustrates the results for Stage 2 amplification using the BIACORE™ optical biosensor. Unlike the dose response curve experiment, binding experiments were conducted with microbubbles in excess and the binding sites on the BIACORE™ surface limiting. When the gold surface was saturated with Stage 1 binding, a signal displacement of 12.5 Response Units (RU) was observed (FIG. 7b). The biotin microbubbles were then converted to neutravidin microbubbles by the addition of neutravidin. Stage 2 amplification was obtained by adding biotinylated microbubbles. The microbubbles were added until saturation was observed (no increase in RU seen). A signal displacement of 46.3 RU was observed for Stage 2 binding. The ratio of Stage II signal displacement to Stage I signal displacement indicates an amplification factor of 3.7.

Example 11

In Vitro Assembly of Multi-Stage Complexes as Observed by Dark Phase Microscopy

In this Example, a polystyrene binding surface was prepared by incubating biotinylated BSA overnight in a polystyrene petri dish; neutravidin was then bound to the biotinylated BSA to form the target site. For Stage 1 binding, biotinylated microbubbles were bound to the neutravidin on the polystyrene surface; this is depicted in FIG. 8.

For Stage 2 binding, neutravidin was allowed to bind to the Stage 1 biotin microbubbles, and biotin microbubbles were then allowed to bind to the Stage 1 neutravidin microbubble complex. Stage 2 binding is depicted in FIG. 9.

For Stage 3 binding, neutravidin was allowed to bind to the Stage 2 biotin microbubbles, and then biotin microbubbles were allowed to bind to the Stage 2 neutravidin microbubble complex. Stage 3 binding is depicted in FIG. 10.

Example 12

In Vitro Demonstration of Stage 2 Amplification

Materials: 60 mm Not TC-Treated culture dishes were obtained from Corning, Inc. (Lowell, Mass.). Targestar B biotinylated microbubbles were obtained from Targesson, Inc. (San Diego, Calif.). A 50 µg/ml biotinylated BGG coating solution was prepared. The center of the petri dish was spotted with 25 µl of the B-BGG solution, and the spot was allowed to dry. A neutravidin (coat)—BSA (block) solution was prepared with a final concentration of 30 µg/ml neutravidin in phosphate buffered saline (PBS) buffer containing 1% BSA. The plate was incubated overnight with the neutravidin-BSA solution with no mixing and then washed with 4 volumes of PBS spiked with TWEEN®20 to 0.075%.

For Stage 1 binding, 50 µl of the biotinylated microbubbles were added to the center of the petri dish, and the plate was inverted and mixed gently by hand for 10 minutes. The plate was then washed with 4 volumes of PBS and photographed at 200× (FIG. 11, left panel).

For Stage 2 binding, 0.2 mM biotin in 1% BSA in PBS was added to the dish, and the plate was mixed gently for one hour to block excess neutravidin sites. After washing with 4×3 ml PBS, the plate was then incubated with 0.15 mM neutravidin in 1% BSA in PBS for 30 minutes, followed by washing 4×3 ml PBS. The added neutravidin converted the biotinylated microbubbles into neutravidin microbubbles. 50 µl microbubbles were added to the center of the petri dish, which was then inverted and hand mixed on a flat surface for 10 minutes. The plate was then washed with 4 volumes PBS. 1 ml PBS was then added, and the plate photographed at 200× (FIG. 11, right panel).

The results shown in FIG. 11 clearly demonstrate amplification of the original target microbubbles.

Thus, in accordance with the present invention, there has been provided compositions for target detection and/or treatment, as well as methods of production and use thereof, that fully satisfy the objectives and advantages set forth hereinabove. Although the inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

REFERENCES

The following references, to the extent that they provide exemplary procedural or other details supplementary to those set forth herein, are specifically incorporated herein by reference.

Accardo et al. (2009) *Coordination Chemistry Reviews*, 253:2193-2213.
Bohmer, et al. (2009) *European Journal of Radiology*, 70:242-253.
Cai et al. (2008) *J Nuclear Med.*, 49(6)
Carter (2001) *Nature*, 1:118.
Dayton, P. (2009) *Proceedings of the Sixth IEEE international conference on Symposium on Biomedical Imaging: From Nano to Macro*, Boston, Mass., USA, 751-753.
Dayton (2002) *Journal of Magnetic Resonance Imaging*, 16:362-377.
de Jong et al. (2009) *Med. Biol. Eng. Comput.*, 47:861-873.
Dimitrov et al. (2009) *Therapeutic Antibodies*, 525:1-27.
Dolan et al. (2009) *Journal of the American College of Cardiology*, 53(1).
Duncan (2006) *Nature*, 6:688-701.
Ferrara et al. (2007) *Annual Review of Biomedical Engineering*, 9:415-447.
Giesecke et al. (2003) *Ultrasound in Med. And Biol.*, 29(9): 1359-1365.
Glazer et al. (2004) *Proc. Intl. Soc. Mag. Reson. Med.* 11:1713.
Greco et al. (2010) *Molecular Therapy*, 18:295-306.
Halpern (2005) *Radiology*, 235:345-346.
Hansen et al. (1995) *Biochimica et Biophysica Acta*, 1239: 133-144.
Hernot et al. (2008) *Advanced Drug Delivery Reviews*, 60(10):1153-1166.
Higgins et al. (2006) *MRI and CT of the Cardiovascular System*, Lippincott, Williams and Wilkins, Philadelphia, Pa. Page 109.
Huang (2008) *Advanced Drug Delivery Reviews*, 60:1167-1176.
Hughes et al. (2003) *Medicamundi*, 47(1):67-73.
Husseini et al. (2008) *Adv. Drug Delivery Rev.*, 60(10):1137-1152.
Immordino et al. (2006) *International Journal of Nanomedicine*, 1(3):297-315.
Kaasgaard et al. (2001) *International Journal of Pharmaceutics*, 214(1-2):63-65.
Kheirolomoom et al. (2007) *Journal of Controlled Release*, 118(3):275-284.
Kim et al. (2009) *Chem. Soc. Rev.*, 38:372-390.
Klibanov (1999) *Advanced Drug Delivery Reviews*, 37:139-157.
Klibanov (2006) *Invest. Radiology*, 41:354-362.
Lanza et al. (1996) *Circulation*, 94:3334-3340.
Lanza et al. (2003) *Curr. Probl. Cardiol.*, 28:625-653.
Latif et al. (1987) *Immunology Letters*, 15:45-51.
Lentacker et al. (2010) *Molecular Therapy*, 18: 101-108.
Lindner (2002) *The American Journal of Cardiology*, 90(10):72-80.
Liu et al. (2006) *Journal of Controlled Release*, 114:89-99.
Macor et al. (2006) *Cancer Res.*, 66(7):3876-3883.
McCarthy et al. (2008) *Adv. Drug Delivery Rev.*, 60:1241-1251.
Miller et al. (2008) *Journal of Ultrasound Medicine*, 27:611-632.
Myhr et al. (2006) *Cancer Letters*, 232:206-213.
Noppl-Simson et al. (1996) *Biophysical Journal*, 70:1391-1401.
Ogihara-Umeda et al. (2007) *International Journal of Pharmaceutics*, 337(1-2):316-328.
Otani et al. (2009) *Circulation*, 120:S328.
Paliwal et al. (2006) *Expert Opinion on Drug Delivery*, 3(6):713-726.
Rieter et al. (2006) *J. Am. Chem. Soc.*, 128(28):9024-9025.
Rivnay et al. (1987) *Methods in Enzymology*, Vol. 149.
Schmitz (2008) *Basic Res Cardiol*, 103:174-181.
Schneider (2008) *J. Endourology*, 22(4):
Schroeder et al. (2009) *Chemistry and Physics of Lipids*, 162:1-16.
Sontum (2008) *Ultrasound in Med. And Biol.*, 34.
Suzuki et al. (2007) *Journal of Controlled Release*, 117: 130-136.
Suzuki et al. (2008) *International Journal of Pharmaceutics*, 354:49-55.
Szoka, Jr. et al. (1978) *Proc. Natl. Acad. Sci. USA*, 75(9): 4194-4198.
Tinkov et al. (2009) *J. Pharm. Sci.*, 98:1935-1961.
Tochilin et al. (2001) *Biochimica et Biophysica Acta—Biomembranes*, 1511(2):397-411.
Unger et al. (2002) *European Journal of Radiology*, 42:160-168.
Unger et al. (2004) *Advanced Drug Delivery Reviews*, 56:1291-1314.
Wright et al. (1989) *Drug Advance Drug Delivery Reviews*, 3:343-389.
Zavaleta et al. (2007) *International Journal of Pharmaceutics*, 337(1-2):316-328.

What is claimed is:

1. A complex of sequentially deliverable pharmaceutical reagents useful for detecting a target exposed in a lumen through imaging, wherein the complex is formed in vivo, the complex comprising:
   a target exposed on a surface of a lumen within a body of a subject;
   at least one targeting vesicle bound to the target;
   a plurality of amplification vesicles, wherein at least two amplification vesicles are directly bound to a single targeting vesicle;
   a plurality of imaging vesicles;
   wherein each of the plurality of imaging vesicles is bound to an amplification vesicle, and wherein at least the imaging vesicles are detectable by an imaging modality, thus allowing detection of the complex bound to the target; and
   wherein the complex is formed in the lumen within the subject's body and bound to the surface of the lumen, and the target exposed in the lumen is detected via the imaging modality present in the complex.

2. The complex of claim 1, wherein two or more imaging vesicles are bound to a single amplification vesicle.

3. The complex of claim 1, wherein the targeting, amplification and imaging vesicles are each selected from the group consisting of liposomes, echogenic liposomes, multimodal echogenic liposomes, microbubbles, microballoons, microspheres, matrix particles, micelles, aggregation based constructs, nanoparticle vesicles, perfluorocarbon nanodroplets, and combinations thereof.

4. The complex of claim 1, wherein at least one of the targeting, amplification, and imaging vesicles comprises a gas.

5. The complex of claim 1, wherein at least one the targeting, amplification, and imaging vesicles further comprises a therapeutic composition incorporated/encapsulated therein.

6. The complex of claim 4, wherein the therapeutic composition is delivered, released, activated and/or excited upon targeting via the targeting vesicle.

7. The complex of claim 5, wherein the release/activation/excitation is in response to exposure to at least one of heat, ultrasound and chemical methods.

8. The complex of claim 1, wherein:
(a) the targeting vesicle is further defined as comprising a primary binding site and a plurality of secondary binding sites;
(b) the amplification vesicle is further defined as comprising at least one tertiary binding site and at least one quaternary binding site;
(c) the imaging vesicle is further defined as comprising at least one quinary binding site;
(d) wherein the primary binding site of the targeting vesicle forms a first binding complex with the target, at least two of the secondary binding sites of the targeting vesicle each forms a second binding complex with the tertiary binding site of an amplification vesicle, and the quaternary binding site of an amplification vesicle forms a third binding complex with the quinary binding site of the imaging vesicle.

9. The complex of claim 7, wherein at least one of:
(a) the tertiary and quaternary binding sites of the amplification vesicle are identical and complementary to each of the plurality of secondary binding sites of the targeting vesicle and the at least one quinary binding site of the imaging vesicle; and
(b) each of the plurality of secondary binding sites of the targeting vesicle is identical to the at least one quaternary binding site of the amplification vesicle, whereby the secondary binding site of the targeting vesicle can also bind the quinary binding site of an imaging vesicle to form the third binding complex.

10. The complex of claim 8, wherein each of the primary, secondary, tertiary, quaternary and quinary binding sites is selected from the group consisting of peptides, proteins, antigens, antibodies, antibody fragments, receptors, ligands, glycoconjugates, and combinations or derivatives thereof.

11. The complex of claim 1, wherein the complex further comprises a second imaging vesicle different from the first imaging vesicle, and wherein a first imaging vesicle and a second imaging vesicle are bound to a single amplification vesicle.

12. The complex of claim 11, wherein the amplification vesicle is provided with two different binding sites to which the first and second imaging vesicles bind.

\* \* \* \* \*